US008530213B2

(12) United States Patent
Bommarius et al.

(10) Patent No.: US 8,530,213 B2
(45) Date of Patent: Sep. 10, 2013

(54) COMPOSITIONS AND METHODS FOR USING NADH OXIDASES

(75) Inventors: Andreas Bommarius, Atlanta, GA (US); Bettina Bommarius, Atlanta, GA (US); Jun-Ichiro Hirano, Atlanta, GA (US); Vaijayanthi Thangavel, Atlanta, GA (US); Jonathan Taejoo Park, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 175 days.

(21) Appl. No.: 12/958,949

(22) Filed: Dec. 2, 2010

(65) Prior Publication Data

US 2012/0003688 A1   Jan. 5, 2012

Related U.S. Application Data

(60) Provisional application No. 61/383,858, filed on Sep. 17, 2010, provisional application No. 61/265,915, filed on Dec. 2, 2009.

(51) Int. Cl.
*C12N 9/02* (2006.01)
*C12P 41/00* (2006.01)
*C12P 1/00* (2006.01)
*C12Q 1/26* (2006.01)

(52) U.S. Cl.
USPC ............... 435/189; 435/280; 435/41; 435/25

(58) Field of Classification Search
USPC ...................... 435/189, 280, 41, 25
See application file for complete search history.

(56) References Cited

U.S. PATENT DOCUMENTS

2011/0252501 A1* 10/2011 Abad et al. .................. 800/275

OTHER PUBLICATIONS

Kleerebezem et al. Complete Genome Sequence of *Lactobacillus plantarum* WCFS1; Proceedings of the National Academy of Science, vol. 100, No. 4 (2003) pp. 1-6.*

* cited by examiner

*Primary Examiner* — Susan Hanley
*Assistant Examiner* — Paul Martin
(74) *Attorney, Agent, or Firm* — Troy S. Kleckley; Ryan A. Schneider, Esq.; Troutman Sanders LLP

(57) ABSTRACT

The present disclosure relates generally to bacterial NADH oxidases and, more particularly, to novel NADH oxidases obtained from *Lactobacillus plantarum*, and derivatives thereof that demonstrate enzymatic activity for NADH, NADPH, or both NADH and NADPH. The compositions comprising an NADH oxidase obtained from *L. plantarum* or derivatives thereof include: isolated enzymes; recombinantly produced enzymes and derivatives thereof, as well as catalytically active portions thereof; nucleic acids encoding an NADH oxidase obtained from *L. plantarum*, derivatives thereof, and portions thereof. The methods of the present invention include isolation of NADH oxidases obtained from *L. plantarum*, derivatives thereof, and portions thereof, and methods for enzymatic reactions comprising NADH oxidase obtained from *L. plantarum*, including the production of enantiomer-enriched organic compounds.

13 Claims, 3 Drawing Sheets

SEQUENCE LISTING

<160> NUMBER OF SEQ ID NOS: 25

<210> SEQ ID NO 1
<211> LENGTH: 450
<212> TYPE: PRT
<213> ORGANISM: Lactobacillus plantarum

<400> SEQUENCE: 1

Met Lys Val Ile Val Ile Gly Cys Thr His Ala Gly Thr Ala Ala Val

```
         1               5                  10                 15
Asn Gln Ile Leu Ala Ser Asn Pro Asp Thr Glu Val Thr Ile Tyr Glu
                20                  25                 30

Arg Asn Asp Asn Val Ser Phe Leu Ser Cys Gly Ile Ala Leu Tyr Leu
                35                  40                 45

Gly Gly Gln Val Ala Asp Pro Gln Gly Leu Phe Tyr Ser Ser Pro Glu
                50                  55                 60

Gln Leu Ala Lys Leu Gly Ala Thr Val His Met Gln His Asp Val Thr
65                  70                  75                 80

Asp Val Asn Thr Asp Lys His Glu Ile Thr Val Thr Asp Leu Lys Thr
                85                  90                 95

Gly Glu Ser Lys Thr Asp His Tyr Asp Lys Leu Val Val Thr Thr Gly
                100                 105                110

Ser Trp Pro Val Ile Pro Pro Ile Asp Gly Ile Asp Ser Pro Asn Val
                115                 120                125

Tyr Leu Cys Lys Asn Trp Thr His Ala Gln Asn Leu Trp Glu Ala Ala
                130                 135                140

Lys Pro Ala Lys Arg Val Ile Val Gly Gly Tyr Ile Gly Thr
145                 150                 155                160

Glu Leu Val Glu Ala Tyr Gln Lys Gln Gly Lys Val Thr Leu Ile
                165                 170                175

Asp Gly Leu Pro Arg Ile Leu Asn Lys Tyr Leu Asp Lys Glu Phe Thr
                180                 185                190

Asp Arg Val Glu Gln Asp Phe Val Asp His Gly Ile Lys Met Ala Leu
                195                 200                205

Asn Gln Met Val Gln Gly Phe Ser Asp Asp Gly Lys Glu Val Thr Val
                210                 215                220

Lys Thr Asp Lys Gly Ser Tyr Thr Ala Asp Met Ala Ile Leu Cys Val
225                 230                 235                240

Gly Phe Arg Pro Asn Thr Gly Leu Leu Lys Gly Lys Val Asp Met Asn
                245                 250                255

Ala Asn Gly Ser Ile Lys Thr Asn Asp Tyr Met Gln Thr Ser Asp Pro
                260                 265                270

Asp Ile Tyr Gly Ala Gly Asp Ser Val Ala Val His Tyr Asn Pro Thr
                275                 280                285

Lys Lys Asp Ala Tyr Ile Pro Leu Ala Thr Asn Ala Val Arg Gln Gly
                290                 295                300

Thr Leu Val Gly Leu Asn Ile Phe Lys Pro Thr Arg Lys Tyr Met Gly
305                 310                 315                320

Thr Gln Ser Thr Ser Gly Leu Met Leu Phe Gly Gln Thr Ile Val Ser
                325                 330                335

Ser Gly Met Thr Leu Glu His Ala Gln Ala Glu Asn Val Pro Ala Ala
                340                 345                350

Ala Val Thr Phe Glu Asp Asn Tyr Arg Pro Glu Phe Met Pro Thr Thr
                355                 360                365

Lys Pro Val Leu Met Gln Leu Val Tyr Asn Pro Glu Thr Arg Glu Ile
370                 375                 380

Leu Gly Ala Gln Phe Met Ser Glu His Asp Val Ser Gln Ser Ala Asn
385                 390                 395                400

Val Ile Ser Val Met Ile Gln Asn His Asn Thr Ile Asp Asp Leu Gly
                405                 410                415

Phe Val Asp Met Phe Phe Gln Pro Ile Tyr Asp Arg Pro Phe Asn Tyr
                420                 425                430
```

Leu Asn Leu Leu Gly Gln Ala Ala Ile Ala His Ala Ala Glu Ala Val
        435                 440                 445

Thr Glu
    450

<210> SEQ ID NO 2
<211> LENGTH: 1353
<212> TYPE: DNA
<213> ORGANISM: Lactobacillus plantarum

<400> SEQUENCE: 2

```
atgaaagtta ttgtaattgg ttgtacccat gccggcactg ctgctgttaa tcagatttta      60
gcatcaaatc cagatactga agtgacgatt tatgaaagaa atgacaatgt ctcgttccta     120
tcctgtggga tcgcacttta ccttggcggc aagttgctg atcctcaagg cctatttta     180
tccagtcctg aacagttagc taagttaggc gcaactgttc atatgcaaca tgatgtgacg     240
gatgtgaata ctgacaaaca tgaaattacg gttactgact aaagactgg tgaatctaag     300
actgatcact atgacaagtt agttgtcact actggttcat ggcctgttat tccaccaatt     360
gacggcatcg atagtcccaa tgtctactta tgcaagaact ggacgcacgc tcagaattta     420
tgggaagcag ccaaaccagc taagcgggtc attgtgatcg gtggcggtta tatcggtact     480
gaattagttg aagcttacca gaagcaaggt aaggaagtca cactaattga tggtttacca     540
cggatttaa ataaatactt agacaaagaa ttcactgacc gggttgaaca agactttgtt     600
gatcacggta tcaagatggc tttgaatcaa atggtgcaag gcttcagtga tgatggtaaa     660
gaagttacgg tcaagactga caagggcagc tacacagccg acatggcgat tctttgtgtt     720
ggcttccggc caaataccgg cttactcaag ggcaaggtcg atatgaacgc taatggctcg     780
atcaagacca tgactacat gcaaacttct gatccagaca tttacggggc tggtgactcg     840
gttgctgttc actataaccc aactaagaaa gatgcttata tcccattagc aacgaatgcg     900
gttcgccaag gaaccttagt tggttttgaac atcttcaagc caacgcggaa gtacatgggg     960
acacaatcaa cttctgggtt aatgttgttc ggccaaacca tcgtttcatc tgggatgacc    1020
ctagaacatg cacaggccga aaatgttccg gcagccgctg tcacttttga agacaactac    1080
cggccagaat ttatgccaac cactaagcct gtttttaatgc aattggttta caatcctgaa    1140
actcgcgaaa tcctaggtgc acaattcatg agtgaacatg atgtttcgca atcagccaat    1200
gtgatttcag tgatgattca aaatcacaat accattgacg acttagggtt cgtagatatg    1260
ttcttccaac caatttacga ccggccattt aactatttga acttacttgg tcaagcagcg    1320
attgcccatg cggccgaagc tgtcactgaa taa                                 1353
```

<210> SEQ ID NO 3
<211> LENGTH: 450
<212> TYPE: PRT
<213> ORGANISM: Lactobacillus plantarum

<400> SEQUENCE: 3

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45

Gly Gly Gln Val Ala Asp Pro Gln Gly Leu Phe Tyr Ser Ser Pro Glu
    50                  55                  60

-continued

```
Gln Leu Ala Lys Leu Gly Ala Thr Val His Met Gln His Asp Val Thr
 65                  70                  75                  80

Asp Val Asn Thr Asp Lys His Glu Ile Thr Val Thr Asp Leu Lys Thr
                 85                  90                  95

Gly Glu Ser Lys Thr Asp His Tyr Asp Lys Leu Val Thr Thr Gly
                100                 105                 110

Ser Trp Pro Val Ile Pro Pro Asp Gly Ile Asp Ser Pro Asn Val
            115                 120                 125

Tyr Leu Cys Lys Asn Trp Thr His Ala Gln Asn Leu Trp Glu Ala Ala
        130                 135                 140

Lys Pro Ala Lys Arg Val Ile Val Ile Gly Gly Tyr Ile Gly Thr
145                 150                 155                 160

Glu Leu Val Glu Ala Tyr Gln Lys Gln Gly Lys Glu Val Thr Leu Ile
                165                 170                 175

Asp Lys Leu Pro Arg Ile Leu Asn Lys Tyr Leu Asp Lys Glu Phe Thr
            180                 185                 190

Asp Arg Val Glu Gln Asp Phe Val Asp His Gly Ile Lys Met Ala Leu
        195                 200                 205

Asn Gln Met Val Gln Gly Phe Ser Asp Asp Gly Lys Glu Val Thr Val
210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                245                 250                 255

Ala Asn Gly Ser Ile Lys Thr Asn Asp Tyr Met Gln Thr Ser Asp Pro
            260                 265                 270

Asp Ile Tyr Gly Ala Gly Asp Ser Val Ala Val His Tyr Asn Pro Thr
        275                 280                 285

Lys Lys Asp Ala Tyr Ile Pro Leu Ala Thr Asn Ala Val Arg Gln Gly
290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
        355                 360                 365

Lys Pro Val Leu Met Gln Leu Val Tyr Asn Pro Glu Thr Arg Glu Ile
370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
            420                 425                 430

Leu Asn Leu Leu Gly Gln Ala Ala Ile Ala His Ala Ala Glu Ala Val
        435                 440                 445

Thr Glu
    450

<210> SEQ ID NO 4
<211> LENGTH: 450
<212> TYPE: PRT
<213> ORGANISM: Lactobacillus plantarum
```

```
<400> SEQUENCE: 4

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45

Gly Gly Gln Val Ala Asp Pro Gln Gly Leu Phe Tyr Ser Ser Pro Glu
    50                  55                  60

Gln Leu Ala Lys Leu Gly Ala Thr Val His Met Gln His Asp Val Thr
65                  70                  75                  80

Asp Val Asn Thr Asp Lys His Glu Ile Thr Val Thr Asp Leu Lys Thr
                85                  90                  95

Gly Glu Ser Lys Thr Asp His Tyr Asp Lys Leu Val Val Thr Thr Gly
            100                 105                 110

Ser Trp Pro Val Ile Pro Pro Ile Asp Gly Ile Asp Ser Pro Asn Val
        115                 120                 125

Tyr Leu Cys Lys Asn Trp Thr His Ala Gln Asn Leu Trp Glu Ala Ala
    130                 135                 140

Lys Pro Ala Lys Arg Val Ile Val Ile Gly Gly Tyr Ile Gly Thr
145                 150                 155                 160

Glu Leu Val Glu Ala Tyr Gln Lys Gln Gly Lys Val Thr Leu Ile
                165                 170                 175

Asp Lys Leu Pro Arg Ile Leu Asn Lys Tyr Leu Asp Lys Glu Phe Thr
        180                 185                 190

Asp Arg Val Glu Gln Asp Phe Val Asp His Gly Ile Lys Met Ala Leu
    195                 200                 205

Asn Gln Met Val Gln Gly Phe Ser Asp Asp Gly Lys Glu Val Thr Val
        210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                245                 250                 255

Ala Asn Gly Ser Ile Lys Thr Asn Asp Tyr Met Gln Thr Ser Asp Pro
            260                 265                 270

Asp Ile Tyr Gly Ala Gly Asp Ser Val Ala Val His Tyr Asn Pro Thr
        275                 280                 285

Lys Lys Asp Ala Tyr Ile Pro Leu Ala Thr Asn Ala Val Arg Gln Gly
    290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
        355                 360                 365

Lys Pro Val Leu Met Gln Leu Val Tyr Asn Pro Glu Thr Arg Glu Ile
    370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415
```

```
Phe Val Asp Met Phe Phe Gln Pro Ile Tyr Asp Arg Pro Phe Asn Tyr
            420                 425                 430

Leu Asn Leu Leu Gly Gln Ala Ala Ile Ala His Ala Ala Glu Ala Val
        435                 440                 445

Thr Glu
    450

<210> SEQ ID NO 5
<211> LENGTH: 1353
<212> TYPE: DNA
<213> ORGANISM: Lactobacillus plantarum

<400> SEQUENCE: 5
atgaaagtta ttgtaattgg ttgtacccat gccggcactg ctgctgttaa tcagattta      60 gcatcaaatc cagatactga agtgacgatt tatgaaagaa atgacaatgt ctcgttccta    120
tcctgtggga tcgcacttta ccttggcggc aagttgctg atcctcaagg cctatttat     180 tccagtcctg aacagttagc taagttaggc gcaactgttc atatgcaaca tgatgtgacg    240
gatgtgaata ctgacaaaca tgaaattacg gttactgact aaagactgg tgaatctaag    300 actgatcact atgacaagtt agttgtcact actggttcat ggcctgttat tccaccaatt   360
gacggcatcg atagtcccaa tgtctactta tgcaagaact ggacgcacgc tcagaattta    420
tgggaagcag ccaaaccagc taagcgggtc attgtgatcg gtggcggtta tatcggtact    480
gaattagttg aagcttacca gaagcaaggt aaggaagtca cactaattga tarrttacca   540 cggatttaa ataaatactt agacaaagaa ttcactgacc gggttgaaca agactttgtt    600
gatcacggta tcaagatggc tttgaatcaa atggtgcaag gcttcagtga tgatggtaaa   660
gaagttacgg tcaagactga caagggcagc tacacagccg acatggcgat tctttgtgtt    720
ggcttccggc caaataccgg cttactcaag ggcaaggtcg atatgaacgc taatggctcg    780
atcaagacca atgactacat gcaaacttct gatccagaca tttacggggc tggtgactcg   840
gttgctgttc actataaccc aactaagaaa gatgcttata tcccattagc aacgaatgcg   900
gttcgccaag gaaccttagt tggttttgaac atcttcaagc caacgcggaa gtacatgggg    960
acacaatcaa cttctgggtt aatgttgttc ggccaaacca tcgtttcatc tgggatgacc   1020
ctagaacatg cacaggccga aaatgttccg gcagccgctg tcactttga agacaactac   1080 cggccagaat ttatgccaac cactaagcct gttttaatgc aattggttta caatcctgaa    1140
actcgcgaaa tcctaggtgc acaattcatg agtgaacatg atgtttcgca atcagccaat   1200
gtgatttcag tgatgattca aaatcacaat accattgacg acttagggtt cgtagatatg   1260
ttcttccaac caatttacga ccggccattt aactatttga acttacttgg tcaagcagcg   1320
attgcccatg cggccgaagc tgtcactgaa taa                                 1353

<210> SEQ ID NO 6
<211> LENGTH: 450
<212> TYPE: PRT
<213> ORGANISM: Lactobacillus plantarum

<400> SEQUENCE: 6

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45
```

-continued

Gly Gly Gln Val Ala Asp Pro Gln Gly Leu Phe Tyr Ser Ser Pro Glu
     50                  55                  60

Gln Leu Ala Lys Leu Gly Ala Thr Val His Met Gln His Asp Val Thr
65                   70                  75                  80

Asp Val Asn Thr Asp Lys His Glu Ile Thr Val Thr Asp Leu Lys Thr
                 85                  90                  95

Gly Glu Ser Lys Thr Asp His Tyr Asp Lys Leu Val Val Thr Thr Gly
             100                 105                 110

Ser Trp Pro Val Ile Pro Pro Ile Asp Gly Ile Asp Ser Pro Asn Val
         115                 120                 125

Tyr Leu Cys Lys Asn Trp Thr His Ala Gln Asn Leu Trp Glu Ala Ala
     130                 135                 140

Lys Pro Ala Lys Arg Val Ile Val Ile Gly Gly Gly Tyr Ile Gly Thr
145                 150                 155                 160

Glu Leu Val Glu Ala Tyr Gln Lys Gln Gly Lys Glu Val Thr Leu Ile
                 165                 170                 175

Asp Gly Lys Pro Arg Ile Leu Asn Lys Tyr Leu Asp Lys Glu Phe Thr
             180                 185                 190

Asp Arg Val Glu Gln Asp Phe Val Asp His Gly Ile Lys Met Ala Leu
         195                 200                 205

Asn Gln Met Val Gln Gly Phe Ser Asp Asp Gly Lys Glu Val Thr Val
     210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                 245                 250                 255

Ala Asn Gly Ser Ile Lys Thr Asn Asp Tyr Met Gln Thr Ser Asp Pro
             260                 265                 270

Asp Ile Tyr Gly Ala Gly Asp Ser Val Ala Val His Tyr Asn Pro Thr
         275                 280                 285

Lys Lys Asp Ala Tyr Ile Pro Leu Ala Thr Asn Ala Val Arg Gln Gly
     290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                 325                 330                 335

Ser Gly Met Thr Leu Glu His Ala Gln Ala Glu Asn Val Pro Ala Ala
             340                 345                 350

Ala Val Thr Phe Glu Asp Asn Tyr Arg Pro Glu Phe Met Pro Thr Thr
         355                 360                 365

Lys Pro Val Leu Met Gln Leu Val Tyr Asn Pro Glu Thr Arg Glu Ile
     370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                 405                 410                 415

Phe Val Asp Met Phe Phe Gln Pro Ile Tyr Asp Arg Pro Phe Asn Tyr
             420                 425                 430

Leu Asn Leu Leu Gly Gln Ala Ala Ile Ala His Ala Ala Glu Ala Val
         435                 440                 445

Thr Glu
450

<210> SEQ ID NO 7
<211> LENGTH: 1353
<212> TYPE: DNA
<213> ORGANISM: Lactobacillus plantarum

<400> SEQUENCE: 7

```
atgaaagtta ttgtaattgg ttgtacccat gccggcactg ctgctgttaa tcagatttta      60
gcatcaaatc cagatactga agtgacgatt tatgaaagaa atgacaatgt ctcgttccta     120
tcctgtggga tcgcacttta ccttggcggc aagttgctg  atcctcaagg cctatttat      180
tccagtcctg aacagttagc taagttaggc gcaactgttc atatgcaaca tgatgtgacg     240
gatgtgaata ctgacaaaca tgaaattacg gttactgact aaagactgg  tgaatctaag     300
actgatcact atgacaagtt agttgtcact actggttcat ggcctgttat tccaccaatt     360
gacggcatcg atagtcccaa tgtctactta tgcaagaact ggacgcacgc tcagaattta     420
tgggaagcag ccaaaccagc taagcgggtc attgtgatcg gtggcggtta tatcggtact     480
gaattagttg aagcttacca gaagcaaggt aaggaagtca cactaattga tggtaaacca     540
cggattttaa ataaatactt agacaaagaa ttcactgacc gggttgaaca agactttgtt     600
gatcacggta tcaagatggc tttgaatcaa atggtgcaag gcttcagtga tgatggtaaa     660
gaagttacgg tcaagactga caagggcagc tacacagccg acatggcgat tctttgtgtt     720
ggcttccggc aaataccgg cttactcaag ggcaaggtcg atatgaacgc taatggctcg     780
atcaagacca atgactacat gcaaacttct gatccagaca tttacggggc tggtgactcg     840
gttgctgttc actataaccc aactaagaaa gatgcttata tcccattagc aacgaatgcg     900
gttcgccaag gaaccttagt tggtttgaac atcttcaagc caacgcggaa gtacatgggg     960
acacaatcaa cttctgggtt aatgttgttc ggccaaacca tcgtttcatc tgggatgacc    1020
ctagaacatg cacaggccga aaatgttccg gcagccgctg tcacttttga agacaactac    1080
cggccagaat ttatgccaac cactaagcct gttttaatgc aattggttta caatcctgaa    1140
actcgcgaaa tcctaggtgc acaattcatg agtgaacatg atgtttcgca atcagccaat    1200
gtgatttcag tgatgattca aaatcacaat accattgacg acttagggtt cgtagatatg    1260
ttcttccaac caatttacga ccggccattt aactatttga acttacttgg tcaagcagcg    1320
attgcccatg cggccgaagc tgtcactgaa taa                                 1353
```

<210> SEQ ID NO 8
<211> LENGTH: 450
<212> TYPE: PRT
<213> ORGANISM: Lactobacillus plantarum

<400> SEQUENCE: 8

```
Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45

Gly Gly Gln Val Ala Asp Pro Gln Gly Leu Phe Tyr Ser Ser Pro Glu
    50                  55                  60

Gln Leu Ala Lys Leu Gly Ala Thr Val His Met Gln His Asp Val Thr
65                  70                  75                  80

Asp Val Asn Thr Asp Lys His Glu Ile Thr Val Thr Asp Leu Lys Thr
                85                  90                  95

Gly Glu Ser Lys Thr Asp His Tyr Asp Lys Leu Val Val Thr Thr Gly
```

```
            100                 105                 110
Ser Trp Pro Val Ile Pro Ile Asp Gly Ile Asp Ser Pro Asn Val
        115                 120                 125

Tyr Leu Cys Lys Asn Trp Thr His Ala Gln Asn Leu Trp Glu Ala Ala
130                 135                 140

Lys Pro Ala Lys Arg Val Ile Val Gly Gly Tyr Ile Gly Thr
145                 150                 155                 160

Glu Leu Val Glu Ala Tyr Gln Lys Gln Gly Lys Glu Val Thr Leu Ile
                165                 170                 175

Asp Gly Arg Pro Arg Ile Leu Asn Lys Tyr Leu Asp Lys Glu Phe Thr
            180                 185                 190

Asp Arg Val Glu Gln Asp Phe Val Asp His Gly Ile Lys Met Ala Leu
        195                 200                 205

Asn Gln Met Val Gln Gly Phe Ser Asp Asp Gly Lys Glu Val Thr Val
                210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                245                 250                 255

Ala Asn Gly Ser Ile Lys Thr Asn Asp Tyr Met Gln Thr Ser Asp Pro
            260                 265                 270

Asp Ile Tyr Gly Ala Gly Asp Ser Val Ala Val His Tyr Asn Pro Thr
        275                 280                 285

Lys Lys Asp Ala Tyr Ile Pro Leu Ala Thr Asn Ala Val Arg Gln Gly
        290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
        355                 360                 365

Lys Pro Val Leu Met Gln Leu Val Tyr Asn Pro Glu Thr Arg Glu Ile
370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
            420                 425                 430

Leu Asn Leu Leu Gly Gln Ala Ala Ile Ala His Ala Ala Glu Ala Val
        435                 440                 445

Thr Glu
    450

<210> SEQ ID NO 9
<211> LENGTH: 450
<212> TYPE: PRT
<213> ORGANISM: Lactobacillus plantarum

<400> SEQUENCE: 9

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
```

```
                    20                  25                  30
Arg Asn Asp Asn Val Ser Phe Leu Ser Cys Gly Ile Ala Leu Tyr Leu
                35                  40                  45

Gly Gly Gln Val Ala Asp Pro Gln Gly Leu Phe Tyr Ser Ser Pro Glu
 50                  55                  60

Gln Leu Ala Lys Leu Gly Ala Thr Val His Met Gln His Asp Val Thr
 65                  70                  75                  80

Asp Val Asn Thr Asp Lys His Glu Ile Thr Val Thr Asp Leu Lys Thr
                85                  90                  95

Gly Glu Ser Lys Thr Asp His Tyr Asp Lys Leu Val Thr Thr Gly
                100                 105                 110

Ser Trp Pro Val Ile Pro Ile Asp Gly Ile Asp Ser Pro Asn Val
                115                 120                 125

Tyr Leu Cys Lys Asn Trp Thr His Ala Gln Asn Leu Trp Glu Ala Ala
    130                 135                 140

Lys Pro Ala Lys Arg Val Ile Val Gly Gly Gly Tyr Ile Gly Thr
145                 150                 155                 160

Glu Leu Val Glu Ala Tyr Gln Lys Gln Gly Lys Glu Val Thr Leu Ile
                165                 170                 175

Asp Gly His Pro Arg Ile Leu Asn Lys Tyr Leu Asp Lys Glu Phe Thr
                180                 185                 190

Asp Arg Val Glu Gln Asp Phe Val Asp His Gly Ile Lys Met Ala Leu
                195                 200                 205

Asn Gln Met Val Gln Gly Phe Ser Asp Gly Lys Glu Val Thr Val
                210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                245                 250                 255

Ala Asn Gly Ser Ile Lys Thr Asn Asp Tyr Met Gln Thr Ser Asp Pro
                260                 265                 270

Asp Ile Tyr Gly Ala Gly Asp Ser Val Ala Val His Tyr Asn Pro Thr
    275                 280                 285

Lys Lys Asp Ala Tyr Ile Pro Leu Ala Thr Asn Ala Val Arg Gln Gly
    290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
                340                 345                 350

Ala Val Thr Phe Glu Asp Asn Tyr Arg Pro Glu Phe Met Pro Thr Thr
    355                 360                 365

Lys Pro Val Leu Met Gln Leu Val Tyr Asn Pro Glu Thr Arg Glu Ile
    370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
                420                 425                 430

Leu Asn Leu Leu Gly Gln Ala Ala Ile Ala His Ala Ala Glu Ala Val
    435                 440                 445
```

Thr Glu
    450

<210> SEQ ID NO 10
<211> LENGTH: 1353
<212> TYPE: DNA
<213> ORGANISM: Lactobacillus plantarum

<400> SEQUENCE: 10

```
atgaaagtta ttgtaattgg ttgtacccat gccggcactg ctgctgttaa tcagatttta      60
gcatcaaatc cagatactga agtgacgatt tatgaaagaa atgacaatgt ctcgttccta     120
tcctgtggga tcgcacttta ccttggcggc aagttgctg atcctcaagg cctatttat      180
tccagtcctg aacagttagc taagttaggc gcaactgttc atatgcaaca tgatgtgacg     240
gatgtgaata ctgacaaaca tgaaattacg gttactgact taaagactgg tgaatctaag     300
actgatcact atgacaagtt agttgtcact actggttcat ggcctgttat tccaccaatt     360
gacggcatcg atagtcccaa tgtctactta tgcaagaact ggacgcacgc tcagaattta     420
tgggaagcag ccaaaccagc taagcgggtc attgtgatcg gtggcggtta tatcggtact     480
gaattagttg aagcttacca gaagcaaggt aaggaagtca cactaattga tggtcrycca     540
cggattttaa ataaatactt agacaaagaa ttcactgacc gggttgaaca agactttgtt     600
gatcacggta tcaagatggc tttgaatcaa atggtgcaag gcttcagtga tgatggtaaa     660
gaagttacgg tcaagactga caagggcagc tacacagccg acatggcgat tctttgtgtt     720
ggcttccggc caaataccgg cttactcaag ggcaaggtcg atatgaacgc taatggctcg     780
atcaagacca tgactacat gcaaacttct gatccagaca tttacggggc tggtgactcg     840
gttgctgttc actataaccc aactaagaaa gatgcttata tcccattagc aacgaatgcg     900
gttcgccaag gaaccttagt tggtttgaac atcttcaagc caacgcggaa gtacatgggg     960
acacaatcaa cttctgggtt aatgttgttc ggccaaacca tcgtttcatc tgggatgacc    1020
ctagaacatg cacaggccga aaatgttccg gcagccgctg tcacttttga agacaactac    1080
cggccagaat ttatgccaac cactaagcct gttttaatgc aattggttta caatcctgaa    1140
actcgcgaaa tcctaggtgc acaattcatg agtgaacatg atgtttcgca atcagccaat    1200
gtgatttcag tgatgattca aaatcacaat accattgacg acttagggtt cgtagatatg    1260
ttcttccaac caatttacga ccggccattt aactatttga acttacttgg tcaagcagcg    1320
attgcccatg cggccgaagc tgtcactgaa taa                                  1353
```

<210> SEQ ID NO 11
<211> LENGTH: 450
<212> TYPE: PRT
<213> ORGANISM: Lactobacillus plantarum

<400> SEQUENCE: 11

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45

Gly Gly Gln Val Ala Asp Pro Gln Gly Leu Phe Tyr Ser Ser Pro Glu
    50                  55                  60

Gln Leu Ala Lys Leu Gly Ala Thr Val His Met Gln His Asp Val Thr
65                  70                  75                  80

-continued

```
Asp Val Asn Thr Asp Lys His Glu Ile Thr Val Asp Leu Lys Thr
                 85                  90                  95
Gly Glu Ser Lys Thr Asp His Tyr Asp Lys Leu Val Val Thr Thr Gly
            100                 105                 110
Ser Trp Pro Val Ile Pro Ile Asp Gly Ile Asp Ser Pro Asn Val
        115                 120                 125
Tyr Leu Cys Lys Asn Trp Thr His Ala Gln Asn Leu Trp Glu Ala Ala
    130                 135                 140
Lys Pro Ala Lys Arg Val Ile Val Gly Gly Tyr Ile Gly Thr
145                 150                 155                 160
Glu Leu Val Glu Ala Tyr Gln Lys Gln Gly Lys Glu Val Thr Leu Ile
                165                 170                 175
Asp Lys Lys Pro Arg Ile Leu Asn Lys Tyr Leu Asp Lys Glu Phe Thr
            180                 185                 190
Asp Arg Val Glu Gln Asp Phe Val Asp His Gly Ile Lys Met Ala Leu
        195                 200                 205
Asn Gln Met Val Gln Gly Phe Ser Asp Asp Gly Lys Glu Val Thr Val
    210                 215                 220
Lys Thr Asp Lys Gly Ser Tyr Thr Ala Asp Met Ala Ile Leu Cys Val
225                 230                 235                 240
Gly Phe Arg Pro Asn Thr Gly Leu Leu Lys Gly Lys Val Asp Met Asn
                245                 250                 255
Ala Asn Gly Ser Ile Lys Thr Asn Asp Tyr Met Gln Thr Ser Asp Pro
            260                 265                 270
Asp Ile Tyr Gly Ala Gly Asp Ser Val Ala Val His Tyr Asn Pro Thr
        275                 280                 285
Lys Lys Asp Ala Tyr Ile Pro Leu Ala Thr Asn Ala Val Arg Gln Gly
    290                 295                 300
Thr Leu Val Gly Leu Asn Ile Phe Lys Pro Thr Arg Lys Tyr Met Gly
305                 310                 315                 320
Thr Gln Ser Thr Ser Gly Leu Met Leu Phe Gly Gln Thr Ile Val Ser
                325                 330                 335
Ser Gly Met Thr Leu Glu His Ala Gln Ala Glu Asn Val Pro Ala Ala
            340                 345                 350
Ala Val Thr Phe Glu Asp Asn Tyr Arg Pro Glu Phe Met Pro Thr Thr
        355                 360                 365
Lys Pro Val Leu Met Gln Leu Val Tyr Asn Pro Glu Thr Arg Glu Ile
    370                 375                 380
Leu Gly Ala Gln Phe Met Ser Glu His Asp Val Ser Gln Ser Ala Asn
385                 390                 395                 400
Val Ile Ser Val Met Ile Gln Asn His Asn Thr Ile Asp Asp Leu Gly
                405                 410                 415
Phe Val Asp Met Phe Phe Gln Pro Ile Tyr Asp Arg Pro Phe Asn Tyr
            420                 425                 430
Leu Asn Leu Leu Gly Gln Ala Ala Ile Ala His Ala Ala Glu Ala Val
        435                 440                 445
Thr Glu
    450

<210> SEQ ID NO 12
<211> LENGTH: 450
<212> TYPE: PRT
<213> ORGANISM: Lactobacillus plantarum

<400> SEQUENCE: 12
```

-continued

```
Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45

Gly Gly Gln Val Ala Asp Pro Gln Gly Leu Phe Tyr Ser Ser Pro Glu
    50                  55                  60

Gln Leu Ala Lys Leu Gly Ala Thr Val His Met Gln His Asp Val Thr
65                  70                  75                  80

Asp Val Asn Thr Asp Lys His Glu Ile Thr Val Thr Asp Leu Lys Thr
                85                  90                  95

Gly Glu Ser Lys Thr Asp His Tyr Asp Lys Leu Val Val Thr Thr Gly
            100                 105                 110

Ser Trp Pro Val Ile Pro Ile Asp Gly Ile Asp Ser Pro Asn Val
        115                 120                 125

Tyr Leu Cys Lys Asn Trp Thr His Ala Gln Asn Leu Trp Glu Ala Ala
    130                 135                 140

Lys Pro Ala Lys Arg Val Ile Val Ile Gly Gly Gly Tyr Ile Gly Thr
145                 150                 155                 160

Glu Leu Val Glu Ala Tyr Gln Lys Gln Gly Lys Glu Val Thr Leu Ile
                165                 170                 175

Asp Arg Lys Pro Arg Ile Leu Asn Lys Tyr Leu Asp Lys Glu Phe Thr
            180                 185                 190

Asp Arg Val Glu Gln Asp Phe Val Asp His Gly Ile Lys Met Ala Leu
        195                 200                 205

Asn Gln Met Val Gln Gly Phe Ser Asp Gly Lys Glu Val Thr Val
    210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                245                 250                 255

Ala Asn Gly Ser Ile Lys Thr Asn Asp Tyr Met Gln Thr Ser Asp Pro
            260                 265                 270

Asp Ile Tyr Gly Ala Gly Asp Ser Val Ala Val His Tyr Asn Pro Thr
        275                 280                 285

Lys Lys Asp Ala Tyr Ile Pro Leu Ala Thr Asn Ala Val Arg Gln Gly
    290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
        355                 360                 365

Lys Pro Val Leu Met Gln Leu Val Tyr Asn Pro Glu Thr Arg Glu Ile
    370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
            420                 425                 430
```

Leu Asn Leu Leu Gly Gln Ala Ala Ile Ala His Ala Ala Glu Ala Val
        435                 440                 445

Thr Glu
    450

<210> SEQ ID NO 13
<211> LENGTH: 1353
<212> TYPE: DNA
<213> ORGANISM: Lactobacillus plantarum

<400> SEQUENCE: 13

```
atgaaagtta ttgtaattgg ttgtacccat gccggcactg ctgctgttaa tcagattta       60 gcatcaaatc cagatactga agtgacgatt tatgaaagaa atgacaatgt ctcgttccta     120
tcctgtggga tcgcactta ccttggcggc aagttgctg atcctcaagg cctatttat       180 tccagtcctg aacagttagc taagttaggc gcaactgttc atatgcaaca tgatgtgacg     240
gatgtgaata ctgacaaaca tgaaattacg gttactgact aaagactgg tgaatctaag     300 actgatcact atgacaagtt agttgtcact actggttcat ggcctgttat tccaccaatt     360
gacggcatcg atagtcccaa tgtctactta tgcaagaact ggacgcacgc tcagaattta     420
tgggaagcag ccaaaccagc taagcgggtc attgtgatcg gtggcggtta tcggtact       480 gaattagttg aagcttacca gaagcaaggt aaggaagtca cactaattga tarraaacca     540
cggattttaa ataaatactt agacaaagaa ttcactgacc gggttgaaca agactttgtt     600
gatcacggta tcaagatggc tttgaatcaa atggtgcaag gcttcagtga tgatggtaaa     660
gaagttacgg tcaagactga caagggcagc tacacagccg acatggcgat tctttgtgtt     720
ggcttccggc aaataccgg cttactcaag ggcaaggtcg atatgaacgc taatggctcg     780
atcaagacca atgactacat gcaaacttct gatccagaca tttacggggc tggtgactcg     840
gttgctgttc actataaccc aactaagaaa gatgcttata tcccattagc aacgaatgcg     900
gttcgccaag gaaccttagt tggtttgaac atcttcaagc aacgcggaa gtacatgggg     960 acacaatcaa cttctgggtt aatgttgttc ggccaaacca tcgtttcatc tgggatgacc    1020
ctagaacatg cacaggccga aaatgttccg gcagccgctg tcacttttga agacaactac    1080
cggccagaat ttatgccaac cactaagcct gttttaatgc aattggttta caatcctgaa    1140
actcgcgaaa tcctaggtgc acaattcatg agtgaacatg atgtttcgca atcagccaat    1200
gtgatttcag tgatgattca aaatcacaat accattgacg acttagggtt cgtagatatg    1260
ttcttccaac caatttacga ccggccattt aactatttga acttacttgg tcaagcagcg    1320
attgcccatg cggccgaagc tgtcactgaa taa                                 1353
```

<210> SEQ ID NO 14
<211> LENGTH: 450
<212> TYPE: PRT
<213> ORGANISM: Lactobacillus plantarum

<400> SEQUENCE: 14

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
            20                  25                  30

Arg Asn Asp Asn Val Ser Phe Leu Ser Cys Gly Ile Ala Leu Tyr Leu
        35                  40                  45

Gly Gly Gln Val Ala Asp Pro Gln Gly Leu Phe Tyr Ser Ser Pro Glu
    50                  55                  60

```
Gln Leu Ala Lys Leu Gly Ala Thr Val His Met Gln His Asp Val Thr
 65                  70                  75                  80

Asp Val Asn Thr Asp Lys His Glu Ile Thr Val Thr Asp Leu Lys Thr
                 85                  90                  95

Gly Glu Ser Lys Thr Asp His Tyr Asp Lys Leu Val Val Thr Thr Gly
            100                 105                 110

Ser Trp Pro Val Ile Pro Ile Asp Gly Ile Asp Ser Pro Asn Val
        115                 120                 125

Tyr Leu Cys Lys Asn Trp Thr His Ala Gln Asn Leu Trp Glu Ala Ala
130                 135                 140

Lys Pro Ala Lys Arg Val Ile Val Ile Gly Gly Gly Tyr Ile Gly Thr
145                 150                 155                 160

Glu Leu Val Glu Ala Tyr Gln Lys Gln Gly Lys Glu Val Thr Leu Ile
                165                 170                 175

Asp Lys Arg Pro Arg Ile Leu Asn Lys Tyr Leu Asp Lys Glu Phe Thr
            180                 185                 190

Asp Arg Val Glu Gln Asp Phe Val Asp His Gly Ile Lys Met Ala Leu
        195                 200                 205

Asn Gln Met Val Gln Gly Phe Ser Asp Asp Gly Lys Glu Val Thr Val
210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
                245                 250                 255

Ala Asn Gly Ser Ile Lys Thr Asn Asp Tyr Met Gln Thr Ser Asp Pro
            260                 265                 270

Asp Ile Tyr Gly Ala Gly Asp Ser Val Ala Val His Tyr Asn Pro Thr
        275                 280                 285

Lys Lys Asp Ala Tyr Ile Pro Leu Ala Thr Asn Ala Val Arg Gln Gly
290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
        355                 360                 365

Lys Pro Val Leu Met Gln Leu Val Tyr Asn Pro Glu Thr Arg Glu Ile
370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
            420                 425                 430

Leu Asn Leu Leu Gly Gln Ala Ala Ile Ala His Ala Ala Glu Ala Val
        435                 440                 445

Thr Glu
    450

<210> SEQ ID NO 15
<211> LENGTH: 450
<212> TYPE: PRT
```

-continued

<213> ORGANISM: Lactobacillus plantarum

<400> SEQUENCE: 15

| | | | | | | | | | | | | | | | |
|---|---|---|---|---|---|---|---|---|---|---|---|---|---|---|---|
| Met | Lys | Val | Ile | Val | Ile | Gly | Cys | Thr | His | Ala | Gly | Thr | Ala | Ala | Val |
| 1 | | | | 5 | | | | | 10 | | | | | 15 | |
| Asn | Gln | Ile | Leu | Ala | Ser | Asn | Pro | Asp | Thr | Glu | Val | Thr | Ile | Tyr | Glu |
| | | | 20 | | | | | 25 | | | | | 30 | | |
| Arg | Asn | Asp | Asn | Val | Ser | Phe | Leu | Ser | Cys | Gly | Ile | Ala | Leu | Tyr | Leu |
| | | | 35 | | | | | 40 | | | | | 45 | | |
| Gly | Gly | Gln | Val | Ala | Asp | Pro | Gln | Gly | Leu | Phe | Tyr | Ser | Ser | Pro | Glu |
| | | 50 | | | | | 55 | | | | | 60 | | | |
| Gln | Leu | Ala | Lys | Leu | Gly | Ala | Thr | Val | His | Met | Gln | His | Asp | Val | Thr |
| 65 | | | | | 70 | | | | | 75 | | | | | 80 |
| Asp | Val | Asn | Thr | Asp | Lys | His | Glu | Ile | Thr | Val | Thr | Asp | Leu | Lys | Thr |
| | | | | 85 | | | | | 90 | | | | | 95 | |
| Gly | Glu | Ser | Lys | Thr | Asp | His | Tyr | Asp | Lys | Leu | Val | Val | Thr | Thr | Gly |
| | | | 100 | | | | | 105 | | | | | 110 | | |
| Ser | Trp | Pro | Val | Ile | Pro | Ile | Asp | Gly | Ile | Asp | Ser | Pro | Asn | Val | |
| | | 115 | | | | | 120 | | | | | 125 | | | |
| Tyr | Leu | Cys | Lys | Asn | Trp | Thr | His | Ala | Gln | Asn | Leu | Trp | Glu | Ala | Ala |
| | 130 | | | | | 135 | | | | | 140 | | | | |
| Lys | Pro | Ala | Lys | Arg | Val | Ile | Val | Gly | Gly | Tyr | Ile | Gly | Thr | | |
| 145 | | | | | 150 | | | | | 155 | | | | | 160 |
| Glu | Leu | Val | Glu | Ala | Tyr | Gln | Lys | Gln | Gly | Lys | Glu | Val | Thr | Leu | Ile |
| | | | | 165 | | | | | 170 | | | | | 175 | |
| Asp | Lys | His | Pro | Arg | Ile | Leu | Asn | Lys | Tyr | Leu | Asp | Lys | Glu | Phe | Thr |
| | | | 180 | | | | | 185 | | | | | 190 | | |
| Asp | Arg | Val | Glu | Gln | Asp | Phe | Val | Asp | His | Gly | Ile | Lys | Met | Ala | Leu |
| | | 195 | | | | | 200 | | | | | 205 | | | |
| Asn | Gln | Met | Val | Gln | Gly | Phe | Ser | Asp | Gly | Lys | Glu | Val | Thr | Val | |
| | 210 | | | | | 215 | | | | | 220 | | | | |
| Lys | Thr | Asp | Lys | Gly | Ser | Tyr | Thr | Ala | Asp | Met | Ala | Ile | Leu | Cys | Val |
| 225 | | | | | 230 | | | | | 235 | | | | | 240 |
| Gly | Phe | Arg | Pro | Asn | Thr | Gly | Leu | Leu | Lys | Gly | Lys | Val | Asp | Met | Asn |
| | | | | 245 | | | | | 250 | | | | | 255 | |
| Ala | Asn | Gly | Ser | Ile | Lys | Thr | Asn | Asp | Tyr | Met | Gln | Thr | Ser | Asp | Pro |
| | | | 260 | | | | | 265 | | | | | 270 | | |
| Asp | Ile | Tyr | Gly | Ala | Gly | Asp | Ser | Val | Ala | Val | His | Tyr | Asn | Pro | Thr |
| | | 275 | | | | | 280 | | | | | 285 | | | |
| Lys | Lys | Asp | Ala | Tyr | Ile | Pro | Leu | Ala | Thr | Asn | Ala | Val | Arg | Gln | Gly |
| | 290 | | | | | 295 | | | | | 300 | | | | |
| Thr | Leu | Val | Gly | Leu | Asn | Ile | Phe | Lys | Pro | Thr | Arg | Lys | Tyr | Met | Gly |
| 305 | | | | | 310 | | | | | 315 | | | | | 320 |
| Thr | Gln | Ser | Thr | Ser | Gly | Leu | Met | Leu | Phe | Gly | Gln | Thr | Ile | Val | Ser |
| | | | | 325 | | | | | 330 | | | | | 335 | |
| Ser | Gly | Met | Thr | Leu | Glu | His | Ala | Gln | Ala | Glu | Asn | Val | Pro | Ala | Ala |
| | | | 340 | | | | | 345 | | | | | 350 | | |
| Ala | Val | Thr | Phe | Glu | Asp | Asn | Tyr | Arg | Pro | Glu | Phe | Met | Pro | Thr | Thr |
| | | 355 | | | | | 360 | | | | | 365 | | | |
| Lys | Pro | Val | Leu | Met | Gln | Leu | Val | Tyr | Asn | Pro | Glu | Thr | Arg | Glu | Ile |
| | 370 | | | | | 375 | | | | | 380 | | | | |
| Leu | Gly | Ala | Gln | Phe | Met | Ser | Glu | His | Asp | Val | Ser | Gln | Ser | Ala | Asn |
| 385 | | | | | 390 | | | | | 395 | | | | | 400 |
| Val | Ile | Ser | Val | Met | Ile | Gln | Asn | His | Asn | Thr | Ile | Asp | Asp | Leu | Gly |

```
                             405                 410                 415
Phe Val Asp Met Phe Phe Gln Pro Ile Tyr Asp Arg Pro Phe Asn Tyr
            420                 425                 430
Leu Asn Leu Leu Gly Gln Ala Ala Ile Ala His Ala Ala Glu Ala Val
            435                 440                 445
Thr Glu
    450

<210> SEQ ID NO 16
<211> LENGTH: 450
<212> TYPE: PRT
<213> ORGANISM: Lactobacillus plantarum

<400> SEQUENCE: 16

Met Lys Val Ile Val Gly Cys Thr His Ala Gly Thr Ala Ala Val
1               5                   10                  15
Asn Gln Ile Leu Ala Ser Asn Pro Asp Thr Glu Val Thr Ile Tyr Glu
                20                  25                  30
Arg Asn Asp Asn Val Ser Phe Leu Ser Cys Gly Ile Ala Leu Tyr Leu
            35                  40                  45
Gly Gly Gln Val Ala Asp Pro Gln Gly Leu Phe Tyr Ser Ser Pro Glu
    50                  55                  60
Gln Leu Ala Lys Leu Gly Ala Thr Val His Met Gln His Asp Val Thr
65                  70                  75                  80
Asp Val Asn Thr Asp Lys His Glu Ile Thr Val Thr Asp Leu Lys Thr
                85                  90                  95
Gly Glu Ser Lys Thr Asp His Tyr Asp Lys Leu Val Val Thr Thr Gly
            100                 105                 110
Ser Trp Pro Val Ile Pro Pro Ile Asp Gly Ile Asp Ser Pro Asn Val
    115                 120                 125
Tyr Leu Cys Lys Asn Trp Thr His Ala Gln Asn Leu Trp Glu Ala Ala
130                 135                 140
Lys Pro Ala Lys Arg Val Ile Val Gly Gly Tyr Ile Gly Thr
145                 150                 155                 160
Glu Leu Val Glu Ala Tyr Gln Lys Gln Gly Lys Glu Val Thr Leu Ile
                165                 170                 175
Asp Arg Arg Pro Arg Ile Leu Asn Lys Tyr Leu Asp Lys Glu Phe Thr
            180                 185                 190
Asp Arg Val Glu Gln Asp Phe Val Asp His Gly Ile Lys Met Ala Leu
    195                 200                 205
Asn Gln Met Val Gln Gly Phe Ser Asp Asp Gly Lys Glu Val Thr Val
210                 215                 220
Lys Thr Asp Lys Gly Ser Tyr Thr Ala Asp Met Ala Ile Leu Cys Val
225                 230                 235                 240
Gly Phe Arg Pro Asn Thr Gly Leu Leu Lys Gly Lys Val Asp Met Asn
                245                 250                 255
Ala Asn Gly Ser Ile Lys Thr Asn Asp Tyr Met Gln Thr Ser Asp Pro
            260                 265                 270
Asp Ile Tyr Gly Ala Gly Asp Ser Val Ala Val His Tyr Asn Pro Thr
    275                 280                 285
Lys Lys Asp Ala Tyr Ile Pro Leu Ala Thr Asn Ala Val Arg Gln Gly
290                 295                 300
Thr Leu Val Gly Leu Asn Ile Phe Lys Pro Thr Arg Lys Tyr Met Gly
305                 310                 315                 320
Thr Gln Ser Thr Ser Gly Leu Met Leu Phe Gly Gln Thr Ile Val Ser
```

```
                            325                 330                 335
Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
            355                 360                 365

Lys Pro Val Leu Met Gln Leu Val Tyr Asn Pro Glu Thr Arg Glu Ile
            370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
            420                 425                 430

Leu Asn Leu Leu Gly Gln Ala Ala Ile Ala His Ala Ala Glu Ala Val
                435                 440                 445

Thr Glu
    450

<210> SEQ ID NO 17
<211> LENGTH: 450
<212> TYPE: PRT
<213> ORGANISM: Lactobacillus plantarum

<400> SEQUENCE: 17

Met Lys Val Ile Val Ile Gly Cys Thr His Ala Gly Thr Ala Ala Val
1               5                   10                  15

Asn Gln Ile Leu Ala Ser Asn Pro Asp Thr Glu Val Thr Ile Tyr Glu
                20                  25                  30

Arg Asn Asp Asn Val Ser Phe Leu Ser Cys Gly Ile Ala Leu Tyr Leu
            35                  40                  45

Gly Gly Gln Val Ala Asp Pro Gln Gly Leu Phe Tyr Ser Ser Pro Glu
        50                  55                  60

Gln Leu Ala Lys Leu Gly Ala Thr Val His Met Gln His Asp Val Thr
65                  70                  75                  80

Asp Val Asn Thr Asp Lys His Glu Ile Thr Val Thr Asp Leu Lys Thr
                85                  90                  95

Gly Glu Ser Lys Thr Asp His Tyr Asp Lys Leu Val Val Thr Thr Gly
            100                 105                 110

Ser Trp Pro Val Ile Pro Pro Ile Asp Gly Ile Asp Ser Pro Asn Val
        115                 120                 125

Tyr Leu Cys Lys Asn Trp Thr His Ala Gln Asn Leu Trp Glu Ala Ala
    130                 135                 140

Lys Pro Ala Lys Arg Val Ile Val Ile Gly Gly Gly Tyr Ile Gly Thr
145                 150                 155                 160

Glu Leu Val Glu Ala Tyr Gln Lys Gln Gly Lys Glu Val Thr Leu Ile
                165                 170                 175

Asp Arg His Pro Arg Ile Leu Asn Lys Tyr Leu Asp Lys Glu Phe Thr
            180                 185                 190

Asp Arg Val Glu Gln Asp Phe Val Asp His Gly Ile Lys Met Ala Leu
        195                 200                 205

Asn Gln Met Val Gln Gly Phe Ser Asp Gly Lys Glu Val Thr Val
    210                 215                 220

Lys Thr Asp Lys Gly Ser Tyr Thr Ala Asp Met Ala Ile Leu Cys Val
225                 230                 235                 240

Gly Phe Arg Pro Asn Thr Gly Leu Leu Lys Gly Lys Val Asp Met Asn
```

```
                245                 250                 255
Ala Asn Gly Ser Ile Lys Thr Asn Asp Tyr Met Gln Thr Ser Asp Pro
            260                 265                 270

Asp Ile Tyr Gly Ala Gly Asp Ser Val Ala Val His Tyr Asn Pro Thr
            275                 280                 285

Lys Lys Asp Ala Tyr Ile Pro Leu Ala Thr Asn Ala Val Arg Gln Gly
            290                 295                 300

Thr Leu Val Gly Leu Asn Ile Phe Lys Pro Thr Arg Lys Tyr Met Gly
305                 310                 315                 320

Thr Gln Ser Thr Ser Gly Leu Met Leu Phe Gly Gln Thr Ile Val Ser
                325                 330                 335

Ser Gly Met Thr Leu Glu His Ala Gln Ala Glu Asn Val Pro Ala Ala
            340                 345                 350

Ala Val Thr Phe Glu Asp Asn Tyr Arg Pro Glu Phe Met Pro Thr Thr
            355                 360                 365

Lys Pro Val Leu Met Gln Leu Val Tyr Asn Pro Glu Thr Arg Glu Ile
            370                 375                 380

Leu Gly Ala Gln Phe Met Ser Glu His Asp Val Ser Gln Ser Ala Asn
385                 390                 395                 400

Val Ile Ser Val Met Ile Gln Asn His Asn Thr Ile Asp Asp Leu Gly
                405                 410                 415

Phe Val Asp Met Phe Phe Gln Pro Ile Tyr Asp Arg Pro Phe Asn Tyr
            420                 425                 430

Leu Asn Leu Leu Gly Gln Ala Ala Ile Ala His Ala Ala Glu Ala Val
            435                 440                 445

Thr Glu
    450

<210> SEQ ID NO 18
<211> LENGTH: 1353
<212> TYPE: DNA
<213> ORGANISM: Lactobacillus plantarum

<400> SEQUENCE: 18
atgaaagtta ttgtaattgg ttgtacccat gccggcactg ctgctgttaa tcagatttta      60
gcatcaaatc cagatactga agtgacgatt tatgaaagaa atgacaatgt ctcgttccta     120
tcctgtggga tcgcacttta ccttggcggc aagttgctg  atcctcaagg cctatttat     180 tccagtcctg aacagttagc taagttaggc gcaactgttc atatgcaaca tgatgtgacg     240
gatgtgaata ctgacaaaca tgaaattacg gttactgact taaagactgg tgaatctaag     300
actgatcact atgacaagtt agttgtcact actggttcat ggcctgttat tccaccaatt     360
gacggcatcg atagtcccaa tgtctactta tgcaagaact ggacgcacgc tcagaattta     420
tgggaagcag ccaaaccagc taagcgggtc attgtgatcg gtggcggtta tatcggtact     480
gaattagttg aagcttacca gaagcaaggt aaggaagtca cactaattga tarrcrycca     540
cggattttaa ataaatactt agacaaagaa ttcactgacc gggttgaaca agactttgtt     600
gatcacggta tcaagatggc tttgaatcaa atggtgcaag cttcagtga  tgatggtaaa     660 gaagttacgg tcaagactga caagggcagc tacacagccg acatggcgat tctttgtgtt     720
ggcttccggc aaataccgg  cttactcaag ggcaaggtcg atatgaacgc taatggctcg     780
atcaagacca tgactacat  gcaaacttct gatccagaca tttacggggc tggtgactcg     840
gttgctgttc actataaccc aactaagaaa gatgcttata tcccattagc aacgaatgcg     900
gttcgccaag gaaccttagt tggtttgaac atcttcaagc caacgcggaa gtacatgggg     960
```

-continued

```
acacaatcaa cttctgggtt aatgttgttc ggccaaacca tcgtttcatc tgggatgacc    1020
ctagaacatg cacaggccga aaatgttccg gcagccgctg tcacttttga agacaactac    1080
cggccagaat ttatgccaac cactaagcct gttttaatgc aattggttta caatcctgaa    1140
actcgcgaaa tcctaggtgc acaattcatg agtgaacatg atgtttcgca atcagccaat    1200
gtgatttcag tgatgattca aaatcacaat accattgacg acttagggtt cgtagatatg    1260
ttcttccaac caatttacga ccggccattt aactatttga acttacttgg tcaagcagcg    1320
attgcccatg cggccgaagc tgtcactgaa taa                                 1353
```

<210> SEQ ID NO 19
<211> LENGTH: 47
<212> TYPE: DNA
<213> ORGANISM: Lactobacillus plantarum

<400> SEQUENCE: 19

```
tgcatgcatg ccatggttat gaaagttatt gtaattggtt gtaccca                   47
```

<210> SEQ ID NO 20
<211> LENGTH: 40
<212> TYPE: DNA
<213> ORGANISM: Lactobacillus plantarum

<400> SEQUENCE: 20

```
ccgccgccgc cgctcgagtt attcagtgac agcttcggcc                           40
```

<210> SEQ ID NO 21
<211> LENGTH: 63
<212> TYPE: DNA
<213> ORGANISM: Lactobacillus plantarum

<400> SEQUENCE: 21

```
gcaaggtaag gaagtcacac taattgatar rttaccacgg attttaaata aatacttaga    60
caa                                                                   63
```

<210> SEQ ID NO 22
<211> LENGTH: 62
<212> TYPE: DNA
<213> ORGANISM: Lactobacillus plantarum

<400> SEQUENCE: 22

```
aggtaaggaa gtcacactaa ttgatggtcr yccacggatt ttaaataaat acttagacaa    60
ag                                                                    62
```

<210> SEQ ID NO 23
<211> LENGTH: 61
<212> TYPE: DNA
<213> ORGANISM: Lactobacillus plantarum

<400> SEQUENCE: 23

```
aggtaaggaa gtcacactaa ttgatggtaa accacggatt ttaaataaat acttagacaa    60
a                                                                     61
```

<210> SEQ ID NO 24
<211> LENGTH: 65
<212> TYPE: DNA
<213> ORGANISM: Lactobacillus plantarum

<400> SEQUENCE: 24

```
gcaaggtaag gaagtcacac taattgatar rcryccacgg attttaaata aatacttaga    60
```

```
caaag                                                                65

<210> SEQ ID NO 25
<211> LENGTH: 64
<212> TYPE: DNA
<213> ORGANISM: Lactobacillus plantarum

<400> SEQUENCE: 25
gcaaggtaag gaagtcacac taattgatar raaaccacgg attttaaata aatacttaga    60
caaa                                                                 64
```

US 8,530,213 B2

COMPOSITIONS AND METHODS FOR USING NADH OXIDASES

CROSS-REFERENCE TO RELATED APPLICATIONS

This application claims, under 35 U.S.C. §119(e), the benefit of U.S. Provisional Application Ser. No. 61/265,915, filed 2 Dec. 2009, and U.S. Provisional Application Ser. No. 61/383,858, filed 17 Sep. 2010, the entire contents and substance of which are hereby incorporated by reference as if fully set forth below.

STATEMENT REGARDING FEDERALLY SPONSORED RESEARCH

This invention was made with U.S. Government support under Grant No. 2 R44AI65127-02 awarded by the National Institutes of Health. The U.S. Government has certain rights in the invention.

BACKGROUND OF THE INVENTION

1. Technical Field

The various embodiments of the present disclosure relate generally to bacterial NADH oxidases and, more particularly, to NADH oxidases obtained from *Lactobacillus plantarum*, and derivatives thereof that demonstrate enzymatic activity for NADH, NADPH, or both NADH and NADPH.

2. Description of Related Art

Enantiomerically pure compounds (EPCs), especially amino and hydroxy acids as well as alcohols, amines, and lactones are increasingly useful in the pharmaceutical, food, and crop protection industries as building blocks for novel compounds not accessible through fermentation as well as for asymmetric synthesis templates. For example, interest in the production of L-nucleosides such as L-ribose, L-mannose and L-glucose has arisen for a number of L-nucleoside-based pharmaceutical compounds. Emtricitabine and Clevudine are some examples of pharmaceutical compounds that are based on L-nucleosides, and a number of these pharmaceuticals are currently approved or in clinical trials.

One advantageous route to a wide variety of EPCs is the use of dehydrogenases, to afford either reduction of keto compounds or oxidation of alcohol or amine groups. The repertoire of dehydrogenases useful for synthesis of EPCs encompasses alcohol dehydrogenases (ADHs), D- and L-lactate dehydrogenases (LDHs), D- or L-hydroxyisocaproate dehydrogenases (D- or L-HicDHs), or amino acid dehydrogenases such as leucine dehydrogenase (LeuDH), phenylalanine dehydrogenase (PheDH), or glutamate dehydrogenase (GluDH). Monooxygenases have been used to synthesize, regio- and enantioselectively, lactones from cyclic ketones useful in the flavor and fragrance industries.

Dehydrogenases and monooxygenases require nicotinamide-based cofactors, such as $NAD^+$ and $NADP^+$ or their reduced equivalents, NADH and NADPH, to function. Economic use of dehydrogenases and cofactor necessitates cofactor regeneration. Cofactor costs, for example, $31 per gram for NAD+ and $232 per gram of $NADP^+$, have to be considered and having cofactors regenerated would cut costs by the turnover number for such cofactors, between 100 and up to 600,000.

Cofactor regeneration with alcohol dehydrogenases can be performed by using the same enzyme for in-situ substrate conversion and cofactor regeneration, usually employing isopropanol as co-substrate, as demonstrated with (S)-ADH from *Thermoanaerobium brockii* for both NADH and NADPH and with (R)-ADH from *L. brevis* for NADPH; this coupled-substrate approach, however, suffers from equilibrium limitations. The more common coupled-system approach, employing a separate second enzyme for regeneration, has been developed for reducing oxidized cofactors, $NAD^+$ or $NADP^+$, to NADH or NADPH. By far the most successful regeneration enzyme is formate dehydrogenase (FDH) for regeneration to either NADPH or NADH, the latter even up to industrial scale. Other options include the use of glucose 6-phosphate dehydrogenase (to NADPH only) or of glucose dehydrogenase, GluDH. For the opposite direction of regeneration, however, from NADPH to oxidized cofactors $NAD^+$ or $NADP^+$, no universally accepted system exists.

For reductive reactions with dehydrogenases or for monooxygenases, NADPH has to be regenerated from $NADP^+$. For this problem, the system formate dehydrogenase (FDH)/formate is now used almost universally, which is shown below:

$$HCOOH+NAD^+ \rightarrow NADH+H^++CO_2 \qquad (1)$$

FDH functions as a universal regeneration enzyme in tandem with dehydrogenases catalyzing extremely enantioselective reduction reactions.

There are some currently known NADH oxidases that are able to oxidize NADH to $NAD^+$ with simultaneous reduction of $O_2$ to either $H_2O_2$ or $H_2O$. Four-electron reduction to benign $H_2O$ is preferred over two-electron reduction to $H_2O_2$, which, even in small amounts, can deactivate either enzyme of the production-regeneration cycle. Addition of catalase as a possible remedy, to degrade the $H_2O_2$, increases complexity of the system to the point where three enzymes have to be coupled and adjusted as to their activity over time.

For oxidative reactions requiring regeneration of $NADP^+$ from NADPH, prior to the present invention, no universal cofactor regeneration system was known. Alcohol dehydrogenase (ADH) itself can be utilized to catalyze both the oxidative production reaction as well as the reductive regeneration reaction by adding isopropanol which is oxidized to acetone, but such a scheme tends to be equilibrium-limited and plagued by deactivation of ADH. Both the ADH and the lactate dehydrogenase (LDH) systems cannot take NADPH, in contrast to glutamate dehydrogenase (GluDH), which has been utilized to reduce α-ketoglutarate to L-glutamate. NADH oxidases from thermophiles have been employed which regenerate NAD+ from NADH by reducing $O_2$ to $H_2O_2$.

What is needed are enzymes that regenerate NADH and NADPH to oxidized cofactors NAD+ and NADP+ and synthesis methods that employ such enzymes alone or in coupled reactions. What is also needed are enzymes that perform the oxidation of NADH to $NAD^+$ with the concomitant reduction of molecular oxygen to water as a solution to the cofactor regeneration problem from NADH to $NAD^+$. Further, what is needed are methods for efficiently isolating the enzymes.

BRIEF SUMMARY OF THE INVENTION

Various embodiments of the present invention are directed to bacterial NADH oxidases and, more particularly, to NADH oxidases obtained from *Lactobacillus plantarum*, and derivatives thereof that demonstrate enzymatic activity for NADH, NADPH, or both NADH and NADPH. A composition of the present invention comprises an isolated bacterial NADH oxidase, which is obtained from *Lactobacillus plantarum*. This isolated bacterial NADH oxidase can comprise the amino acid sequence of SEQ ID NO: 1, which is encoded by a nucleic acid sequence comprising SEQ ID NO: 2. Such a nucleic acid sequence can be incorporated into a vector, which may in turn be introduced into a host cell.

In one embodiment of the present invention, isolated bacterial NADH oxidases obtained from *Lactobacillus plantarum* can regenerate NAD+. In another embodiment of the present invention, isolated bacterial NADH oxidases derived from *Lactobacillus plantarum* can regenerate NADP+. In yet another embodiment of the present invention, isolated bacterial NADH oxidases derived from *Lactobacillus plantarum* can regenerate both NADP+ and NAD+.

For example, an isolated bacterial NADH oxidases derived from *Lactobacillus plantarum*, which regenerates NADP+ or both NADP+ and NAD+, comprises SEQ ID NO: 1, wherein SEQ ID NO: 1 comprises at least one amino acid mutation that facilitates enzymatic activity towards NADPH. A nucleic acid sequence that encodes a NADH oxidases derived from *Lactobacillus plantarum*, which regenerates NADP+ or both NADP+ and NAD+ can hybridize under stringent conditions to the nucleic acid comprising SEQ ID NO: 2.

An isolated bacterial NADH oxidases derived from *Lactobacillus plantarum*, which regenerates NADP+ or both NADP+ and NAD+, can comprise an amino acid sequence selected from the group consisting of SEQ ID NO: 3, SEQ ID NO: 4, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 16, and SEQ ID NO: 17. In an exemplary embodiment, an isolated bacterial NADH oxidases derived from *Lactobacillus plantarum*, which regenerates NADP+ or both NADP+ and NAD+, can comprise an amino acid sequence of SEQ ID NO: 8 or SEQ ID NO: 16

Examples of nucleic acid sequences that encode a NADH oxidases derived from *Lactobacillus plantarum*, which regenerates NADP+ or both NADP+ and NAD+ that can hybridize under stringent conditions to the nucleic acid comprising SEQ ID NO: 2, include, but are not limited to nucleic acid sequences selected from the group consisting of SEQ ID NO: 5, SEQ ID NO: 7, SEQ ID NO: 10, SEQ ID NO: 13, and SEQ ID NO: 18. In an exemplary embodiment, an isolated bacterial NADH oxidases derived from *Lactobacillus plantarum*, which regenerates NADP+ or both NADP+ and NAD+, can be encoded by a nucleic acid sequence comprising SEQ ID NO: 10 or SEQ ID NO: 18.

Another aspect of the present invention comprises a method of producing an enantiomer-enriched organic compound, comprising: reacting a substrate with a first enzyme selective for producing an enantiomer, wherein the first enzyme requires a oxidized nicotinamide-based cofactor for catalytic activity; producing the enantiomer, its oxidized counterpart, and a reduced nicotinamide-based cofactor; and oxidizing the reduced nicotinamide-based cofactor with a second enzyme selective for a nicotinamide-based cofactor. In one embodiment of the present invention, the enantiomer comprises an L-nucleoside, and the second enzyme selective for a nicotinamide-based cofactor comprises a NADH oxidase obtained from *Lactobacillus plantarum*. In another embodiment of the present invention, the second enzyme selective for a nicotinamide-based cofactor can catalyze more than 113,000 turnovers per active site. In yet another embodiment of the present invention, the second enzyme selective for a nicotinamide-based cofactor can catalyze more than 100,000 turnovers per active site in the absence of an externally added reducing agent.

In this method, the NADH oxidase obtained from *Lactobacillus plantarum* can comprise SEQ ID NO: 1. In one embodiment of the present invention, isolated bacterial NADH oxidases obtained from *Lactobacillus plantarum* can regenerate NAD+. In another embodiment of the present invention, isolated bacterial NADH oxidases derived from *Lactobacillus plantarum* can regenerate NADP+. In yet another embodiment of the present invention, isolated bacterial NADH oxidases derived from *Lactobacillus plantarum* can regenerate both NADP+ and NAD+. The isolated bacterial NADH oxidases derived from *Lactobacillus plantarum*, which regenerates NADP+ and NAD+, can comprise an amino acid sequence selected from the group consisting of SEQ ID NO: 3, SEQ ID NO: 4, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 16, or SEQ ID NO: 17. In an exemplary embodiment, the second enzyme selective for a nicotinamide-based cofactor comprises SEQ ID NO: 8 or SEQ ID NO: 18.

Other aspects and features of embodiments of the present invention will become apparent to those of ordinary skill in the art, upon reviewing the following description of specific, exemplary embodiments of the present invention in conjunction with the accompanying figures.

DETAILED DESCRIPTION OF THE INVENTION

Figure 1:
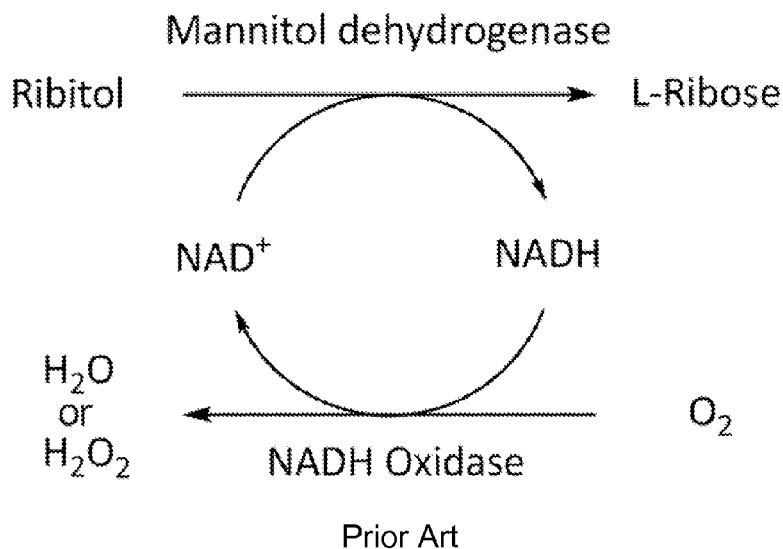
FIG. 1 is a schematic illustrating the conversion of ribitol to L-ribose through mannitol-1-dehydrogenase from *Apium graveolens* complemented with NADH cofactor regeneration using NADH oxidase.

Throughout this description, various components can be identified as having specific values or parameters, however, these items are provided as exemplary embodiments. Indeed, the exemplary embodiments do not limit the various aspects and concepts of the present invention as many comparable parameters, sizes, ranges, and/or values can be implemented. The terms "first," "second," and the like, "primary," "secondary," and the like, do not denote any order, quantity, or importance, but rather are used to distinguish one element from another. Further, the terms "a," "an," and "the" do not denote a limitation of quantity, but rather denote the presence of "at least one" of the referenced item.

In general, NADH oxidases (E.C. 1.6.-.-) catalyze the oxidation of NADH by simultaneously reducing molecular $O_2$ to either hydrogen peroxide, $H_2O_2$, in a two-electron reduction (reaction 2), or directly to water in a four-electron reduction (reaction 3).

$$NADH + O_2 + H^+ \rightarrow NAD^+ + H_2O_2 \qquad (2)$$

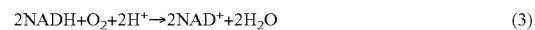

$$2NADH + O_2 + 2H^+ \rightarrow 2NAD^+ + 2H_2O \qquad (3)$$

NADH oxidases contain a second cofactor, presumably covalently bound FAD, as evidenced by the consensus sequence GXT(H/S)AG near the N-terminus, and are widespread among different, evolutionary distinct organisms, such as humans, vertebrates, plants, *Drosophila* and different strains of bacteria. Bacteria harbor both $H_2O_2$-forming and $H_2O$-forming NADH-oxidases. Owing to the deactivation of almost all proteins upon the exposure to $H_2O_2$, the $H_2O$-forming enzymes are superior as biocatalysts. Addition of catalase could potentially destroy the $H_2O_2$ formed, however, catalase itself features a very high $K_M$-value of 1.1 M, so that the enzyme is not particularly active at low $H_2O_2$ concentrations. Thermophilic bacteria usually only feature peroxide-producing NADH oxidases, which, despite their superior stability, render them unfavorable for catalytic purposes. Water-producing NADH-oxidases can be found in various organisms, such as *Streptococcus, Enterococcus, Lactobacillus, Mycobacterium, Methanococcus,* or *Leuconostoc.* These organisms can contain both water- as well as peroxide-producing enzymes.

The various embodiments of the present invention provide novel bacterial NADH oxidases. More specifically, the various embodiment of the present invention provide an NADH oxidase obtained from *Lactobacillus plantarum*, and derivatives thereof that demonstrate enzymatic activity for NADH, NADPH, or for both NADH and NADPH. The compositions comprising an NADH oxidase obtained from *L. plantarum* or derivatives thereof include: isolated enzymes; recombinantly produced enzymes and derivatives thereof, as well as catalytically active portions thereof; nucleic acids encoding an NADH oxidase obtained from *L. plantarum*, derivatives thereof, and portions thereof; vectors and plasmids comprising an NADH oxidase obtained from *L. plantarum*, derivatives thereof, and portions thereof; cells (i.e., prokaryotic or eukaryotic) comprising enzymes or nucleic acids encoding an NADH oxidase obtained from *L. plantarum*, derivatives thereof, and portions thereof. Compositions also include products made in enzymatic reactions in which an NADH oxidase obtained or derived from *L. plantarum* regenerates nicotinamide-based cofactors in the production of enantiomer-enriched organic compounds. The methods of the present invention include isolation of NADH oxidase obtained from *L. plantarum*, derivatives thereof, and portions thereof, and methods for enzymatic reactions comprising NADH oxidase obtained from *L. plantarum*.

As used herein, the term "NADH oxidase, which is obtained from *L. plantarum*" is understood to include the NADH oxidases isolated from *L. plantarum*, which are capable of oxidizing (sometimes referred to as "regenerating") NADH. An example of such an isolated NADH oxidase obtained from *L. plantarum* is illustrated by SEQ ID NO: 1. The term "NADH oxidase, which is obtained from *L. plantarum*" also encompasses an amino acid sequence that encodes an enzyme exhibiting oxidase activity for NADH that has substantial homology to SEQ ID NO 1. As used herein, the term "substantial homology" of an amino acid sequence means that an amino acid sequence includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, as compared to a reference sequence (e.g., SEQ ID NO: 1), provided that the enzymatic activity is retained or the purpose of the sequence is retained, e.g. coding for a protein having a specific enzymatic activity or a protein fragment having a particular binding capability or immunogenic capability.

An NADH oxidase obtained from *L. plantarum* can be encoded by a nucleic acid sequence that encodes an enzyme with oxidase activity for NADH, such as that described in SEQ ID NO: 2. The purified nucleic acid sequence encoding an enzyme exhibiting oxidase activity has substantial homology to SEQ ID NO 2. As used herein, the term "substantial homology" of a nucleic acid sequence means that a nucleic acid sequence includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, as compared to a reference sequence (e.g., SEQ ID NO: 2).

As used herein, the term "NADH oxidase, which is derived from *L. plantarum*" is understood to include derivatives of a NADH oxidase isolated from *L. plantarum* that are capable of oxidizing NADH, NADPH, or both NADH and NADPH. NADH oxidases derived from *L. plantarum* include recombinant nucleic acid sequences derived from the bacterial oxidases of *L. plantarum*, recombinant proteins and peptides expressed by those sequences in heterologous hosts, and any nucleic acid or amino acid variants, mutants, or portions thereof (e.g., catalytically active portions) of bacterial oxidases from *L. plantarum* that are capable of oxidizing NADH, NADPH, or both NADH and NADPH. Thus, NADH oxidases, which are derived from *L. plantarum*, can include proteins and recombinant constructs having altered sequences obtained by mutational methods. Embodiments of mutations of the sequences and resulting proteins disclosed herein also include, but are not limited to, substitutions, insertions, deletions, additions, reversions, changes due to recombination, and other mutations known to those skilled in the art.

In one embodiment of the present invention, an NADH oxidase that is derived from *L. plantarum* can comprise SEQ ID NO: 1, wherein SEQ ID NO: 1 comprises at least one amino acid mutation that facilitates enzymatic activity towards NADPH. In another embodiment, an NADH oxidase that is derived from *L. plantarum* can comprise SEQ ID NO: 1, wherein SEQ ID NO: 1 comprises more than one amino acid mutation that facilitates enzymatic activity towards NADPH. One or more mutations to the amino acid sequence for an NADH oxidase that is derived from *L. plantarum* can confer enzyme activity to only NADH, to only NADPH, or to both NADH and NADPH.

In one embodiment, an NADH oxidase that is derived from *L. plantarum* may include amino acid mutations to accommodate the negative charge associated with the phosphate moiety of NADPH so as to confer enzymatic activity for NADPH. Basic amino acids, such as arginine, lysine, and histidine, are preferred residues for substitution at amino acid residue 178, which is a glycine in the native enzyme, and amino acid residue 179, which is a leucine in the native enzyme. Consequently, amino acid residues 178 and 179 may be mutated to any one basic amino acid and various combinations therebetween. Examples of such NADH oxidase derivatives include G178K (SEQ ID NO: 3), G178R (SEQ ID NO: 4), L179K (SEQ ID NO: 6), L179R (SEQ ID NO: 8), L179H (SEQ ID NO: 9), G178K/L179K (SEQ ID NO: 11), G178R/L179K (SEQ ID NO: 12), G178K/L179R (SEQ ID NO: 14), G178K/L179H (SEQ ID NO: 15), G178R/L179R (SEQ ID NO: 16), and G178R/L179H (SEQ ID NO: 17). These NADH oxidase derivatives are encoded by nucleic acids including G178K/R (SEQ ID NO: 5), L179K (SEQ ID NO: 7), L179R/H (SEQ ID NO: 10), G178K/R/L179K (SEQ ID NO: 13), and G178K/R/L179R/H (SEQ ID NO: 18).

The present invention also comprises nucleic acids that hybridize under stringent conditions with the single-stranded nucleic acids or their complementary single stranded nucleic acids of the present invention. Stringent conditions are well known to those skilled in the art; see Sambrook et al., (Molecular Cloning, A Laboratory Manual, Cold Spring Harbor Laboratory Press (1989), 1.101-1.104). Stringent conditions are established by conditions such as salt concentrations, temperature and amount of time for washing of the hybridized nucleic acids. For example, conditions include washing of hybridized nucleic acids in 0.1% SDS and 1.0× to 0.2×SSC, at temperatures from 50° C. to 68° C., for times of 0.5 to 1.0 hours.

The nucleic acids of the present invention can be incorporated into a vector. The term "vector" as used herein can refer to a cloning vector or an expression vector. A cloning vector refers to a plasmid, phage DNA, a cosmid, or other DNA molecule that is able to replicate autonomously in a host cell. A cloning vector is characterized by one or a number of restriction endonuclease recognition sites at which such DNA sequences may be cut in a determinable fashion without loss of an essential biological function of the vector, and into which a DNA fragment (e.g., SEQ ID NO: 2) may be spliced in order to bring about its replication and cloning. The cloning vector may further contain a marker suitable for use in the identification of cells transformed with the cloning vector (e.g., an antibiotic resistance marker).

An expression vector is similar to a cloning vector but is capable of expressing a gene which has been cloned into it, after transformation into a host. The cloned gene is usually placed under the control of (i.e., operably linked to) a variety of elements for controlling expression of the gene, including promoter sequences, transcription initiation sequences, enhancer sequences, selectable elements, and reporter genes. Examples of suitable expression vectors include, but are not limited to, plasmids, phagemids, cosmids, artificial chromosomes, such as a yeast artificial chromosome (YAC), a bacterial artificial chromosome (BAC), or a P1-derived artificial chromosome (PAC), and bacteriophages, such as lambda phage or M13 phage.

The present invention comprises compositions comprising NADH oxidases obtained or derived from derived from *L. plantarum* and methods of making and using such oxidases, wherein the oxidases regenerate NAD+, NADP+, or NAD+ and NADP+. The ability of an oxidase to oxidize one or both of these cofactors renders it an extremely useful catalyst for coupled enzymatically-catalyzed oxidations. Thus, the present invention comprises bacterial oxidases that regenerate both NADP+ and NAD+. The present invention also comprises novel NADH oxidases that reduce oxygen directly to water, which also makes such enzymes useful in coupled enzymatic reactions.

The NADH oxidases of the present invention participate in enzymatic reactions where there is a conversion of a substrate into a product. In a particularly preferred embodiment of the present invention, the product comprises an enantiomer-enriched organic compound. Consequently, the substrate can include a racemic mixture, such as an alcohol to a ketone, and upon enzymatic reaction will result in a highly enantiomer-enriched unreacted optical antipode of the original molecule, such as an alcohol. Dehydrogenases are capable of very specific enantiomeric selection and are used to prepare enantiomerically pure alcohols, hydroxy acids and amino acids as well as the corresponding ketones and keto acids. The dehydrogenase reaction requires the regeneration of the NADH or NADPH for cofactor activity, and thus, the NADH oxidases of the present invention have utility in coupled reactions with dehydrogenases including, but not limited to, alcohol dehydrogenase, lactate dehydrogenase and amino acid dehydrogenase. Products from such reactions include the resolution of racemic mixtures, such resolution dependent on the selectivity of the dehydrogenase used, and resulting in the unreacted racemate from the original racemic mixture, and the product of the enzyme reaction. For example, from a racemic mixture of an R/S-alcohol, in a reaction with an S-alcohol dehydrogenase, the resulting products are the unreacted enantiomer, the R-alcohol, and the resulting product, e.g., a ketone.

The NADH oxidases of the present invention are involved in synthesis methods comprising enzyme reactions where the substrates have one or more chiral centers. An embodiment of the present invention comprises a method of producing an enantiomer-enriched organic compound, comprising: reacting a substrate with a first enzyme selective for producing an enantiomer, wherein the first enzyme requires an oxidized nicotinamide-based cofactor for catalytic activity; producing the enantiomer and a reduced nicotinamide-based cofactor; and oxidizing the reduced nicotinamide-based cofactor with a second enzyme selective for a nicotinamide-based cofactor. In such methods, the second enzyme selective for a nicotinamide-based cofactor comprises a NADH oxidase obtained or derived from *L. plantarum*. The oxidized nicotinamide-based cofactors can include NAD+, NADP+, or both NAD+ and NADP+. Embodiments of the present invention comprise isolated bacterial oxidases derived from *L. plantarum* that use NADH and NADPH as a cofactor. In a preferred embodiment, isolated bacterial oxidases derived from *L. plantarum* that use NADH and NADPH as a cofactor include SEQ ID NO: 8 or SEQ ID NO: 16.

The compositions of the present invention also comprise combinations of all or a portion of one or more of SEQ ID NO: 2, SEQ ID NO: 5, SEQ ID NO: 7, SEQ ID NO: 10, SEQ ID NO: 13, and SEQ ID NO: 18 with other nucleic acid sequences to encode chimera proteins, or the nucleic acids of NADH oxidases combined with proteins or attached to solid supports such as beads. Such chimera proteins or other combinations may or may not retain the enzyme activity of NADH oxidases. For example, a nucleic acid construct that codes for a chimera protein is constructed from SEQ. ID NO: 2 and sequences for an antibody protein or binding fragment thereof. Such a chimera can be used in antibody labeling experiments.

The present invention also comprises compositions comprising the NADH oxidases disclosed herein that include immobilization of the enzymes on heterogeneous substrates. For example, the enzymes may be immobilized or attached to other proteins, through methods such as chemical linking of the proteins, attached to inert substrates such as microtiter plates, chromatography materials, balls, beads or other substances. The invention contemplates the use of such immobilized enzymes in methods of synthesis, measurement, analysis or other methods wherein enzymes are used. These methods for immobilizing and using such immobilized enzymes are known to those skilled in the art.

The compositions of the present invention also comprise antibodies and other specific binding partners, such as substrates, of NADH oxidases, and immunogenic epitopes thereof. Such antibodies may be polyclonal or monoclonal, and include fragments such as Fab, FC, heavy chains, light chains, constant, variable, or hypervariable fragments or regions, and any type of antibody include but are not limited to IgM, IgG, IgA, IgD, and IgE.

The compositions of the present invention also contemplate the inclusion of any cofactors, metals or other compounds or molecules necessary for activity or stability of the NADH oxidases of the present invention. However, it should be noted that the NADH oxidases of the present invention demonstrate stability in the absence of an exogenous reducing agent, such as dithiothreitol (DTT) or β-mercaptoethanol.

The present invention also comprises host cells comprising the nucleic acids disclosed herein, particularly SEQ ID NO: 2, SEQ ID NO: 5, SEQ ID NO: 7, SEQ ID NO: 10, SEQ ID NO: 13, and SEQ ID NO: 18. Examples of such host cells include, but are not limited to, prokaryotes or eukaryotes, such as *Pseudomonas, Streptomyces, Arthrobacter, Bacillus, Staphylococcus, Enterococcus*, especially *Escherichia coli, Candida, Hansenula, Pichia* and various eukaryotic cells using for example viral-based expression systems. The host cells in which the nucleic acids are cloned are useful for propagation and production of a sufficient amount of the recombinant enzyme or enzymes. The methods for cloning, propagating and producing recombinant proteins in cellular systems are well known in the art.

The nucleic acids disclosed herein that code for the NADH oxidases as described herein, are preferably suitable for the production of whole-cell catalysts. The invention provides a whole-cell catalyst containing a cloned gene for a first enzyme selective for producing an enantiomer (e.g., a dehydrogenase) and a cloned gene for a NADH oxidase, as disclosed herein. The whole-cell catalyst according to one embodiment of the invention can comprise a NADH oxidase, preferably a bacterial oxidase obtained or derived from *L. plantarum* that can regenerate NAD+, NADP+, or both NAD+ and NADP+. More preferably, the NADH oxidase is one or more of the NADH oxidases disclosed herein and encoded for by SEQ ID NO: 2, SEQ ID NO: 5, SEQ ID NO: 7, SEQ ID NO: 10, SEQ ID NO: 13, and SEQ ID NO: 18. The production of such an organism is known to the person skilled in the art as disclosed in PCT/EP00/08473 and PCT/US00/08159, which are hereby incorporated by reference.

The advantage of such an organism is the simultaneous expression of at least two different enzymes, and as a result the whole cell catalyst recombinant organism is only used for the enzymatic reaction. In order to match the expression of the enzymes with respect to their reaction rates, the coding nucleic acids may be cloned into various plasmids having different copy numbers and/or promoters of different strengths. In one embodiment, the enzymes are encoded on plasmids with similar copy numbers in a host cell and/or under the control of promoters of similar strength. With enzyme systems matched in this way there is advantageously no accumulation of a possible inhibiting intermediate compound(s), and the reaction under consideration may proceed at an optimal overall rate.

Methods of the present invention comprise methods for growing and isolating bacterial NADH oxidases, particularly bacterial oxidases obtained or derived from *L. plantarum* capable of regenerating NAD+, NADP+, or both NAD+ and NADP+. One embodiment comprises growing host organisms, such as *Lactobacillus plantarum*, and isolating the NADH oxidases by methods known to those skilled in the art, such as ammonium or acid precipitation, chromatography methods, and other protein purification techniques.

The nucleic acids according to the invention can be used for the production of recombinant NADH oxidases, which is include NADH oxidases obtained or derived from *L. plantarum*. Recombinant techniques known in the art can be used to produce the enzymes described herein in an amount sufficient for an industrial process from host cells carrying the nucleic acids encoding the enzyme of interest. The production of the recombinant enzymes according to the invention is carried out by genetic engineering processes as described in, for example, Sambrook supra, Balbas P & Bolivar F. 1990; Design and construction of expression plasmid vectors in *E. coli*, Methods Enzymology 185, 14-37; Vectors: A Survey of Molecular Cloning Vectors and Their Uses. R. L. Rodriguez & D. T. Denhardt, Eds: 205-225). With regard to the general procedure (PCR and fusion PCR, inverse PCR, cloning, expression etc.), reference may be made to the following literature and the references cited therein: Riley J, Butler R, Finniear R, Jenner D, Powell S, Anand R, Smith J C, Markham A F (1990). A novel, rapid method for the isolation of terminal sequences from yeast artificial chromosome (YAC) clones. Nucl Acids Res. 18, 8186; Triglia T, Peterson M G, Kemp D J (1988). A procedure for in vitro amplification of DNA segments that lie outside the boundaries of known sequences. Nucleic Acids Res. 16, 8186; Sambrook J, Fritsch E F, Maniatis T (1989). Molecular Cloning. Cold Spring Harbour Laboratory Press; Vectors: A Survey of Molecular Cloning Vectors and Their Uses. R. L. Rodriguez & D. T. Denhardt, II.

The bacterial oxidase enzymes described herein may be used in the free form as homogeneously purified compounds, or as enzymes produced by recombinant technology. Furthermore the enzymes may also be employed as a constituent of an intact host organism or in conjunction with the macerated cell mass of the host organism purified to an arbitrarily high degree. It is also possible to use the enzymes in immobilized form (Bhavender P. Sharma, Lorraine F. Bailey and Ralph A. Messing, "Immobilisierte Biomaterialien—Techniken and Anwendungen", Angew. Chem. 1982, 94, 836-852). The immobilization is preferably carried out by lyophilisation (Dordick et al. J. Am. Chem. Soc. 194, 116, 5009-5010; Okahata et al. Tetrahedron Lett. 1997, 38, 1971-1974; Adlercreutz et al. Biocatalysis 1992, 6, 291-305). It is most particularly preferred to carry out the lyophilisation in the presence of surfactants such as aerosol OT, polyvinylpyrrolidone, polyethylene glycol (PEG) or Brij 52 (diethyleneglycolmonocetyl ether) (Goto et al. Biotechnol. Techniques 1997, 11, 375-378). The use as CLECs is also possible (St Clair et al. Angew Chem Int Ed Engl 2000 January, 39(2), 380-383).

The present invention also comprises using NADH oxidases obtained or derived from *L. plantarum* having NAD+, NADP+, or both NAD+ and NADP+ regeneration activity (e.g., G178K (SEQ ID NO: 3), G178R (SEQ ID NO: 4), L179K (SEQ ID NO: 6), L179R (SEQ ID NO: 8), L179H (SEQ ID NO: 9), G178K/L179K (SEQ ID NO: 11), G178R/L179K (SEQ ID NO: 12), G178K/L179R (SEQ ID NO: 14), L179R (SEQ ID NO: 16), G178R/L179R (SEQ ID NO: 16), G178K/L179H (SEQ ID NO: 15), G178R/L179R (SEQ ID NO: 16), and G178R/L179H (SEQ ID NO: 17). These NADH oxidase derivatives are encoded by nucleic acids including G178K/R (SEQ ID NO: 5), L179K (SEQ ID NO: 7), L179R/H (SEQ ID NO: 10), G178K/R/L179K (SEQ ID NO: 13), and G178K/R/L179R/H (SEQ ID NO: 18)) and any mutations thereof, for the production of chiral enantiomer-enriched organic compounds such as, for example, alcohols, amino acids, or nucleosides, in coupled enzymatic reactions. Such compounds are useful in pharmaceutical preparations, in agricultural uses, for food, and crop protection industries as well as building blocks for novel compounds not accessible through fermentation and for asymmetric synthesis templates. For example, compounds are produced that are effective in treatment of humans and other animals for hypertension, diabetes, cardiovascular disease, cancer, infectious disease, and conditions involving the brain, eyes, heart, lungs, liver, immune system, urinary organs, reproductive organs, integumentary system, nervous system and other conditions where pharmaceutical agents are effective.

All patents, patent applications, and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure. Therefore, while embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLES

Example 1

NADH Oxidase Isolated from *Lactobacillus plantarum*

Among the different systems that can be chosen for cofactor regeneration, the use of NADPH oxidases standout with a number of advantages. NADPH oxidases utilize NADPH and oxygen as co-substrates, both which would not needed to be added externally for a regeneration system. (FIG. 1). This would prevent complication of the system by introducing additional substrates. The reaction would either produce water or hydrogen peroxide as final products, and the latter can be easily eliminated through the use of catalases.

Overoxidation of the catalytically active cysteine residue has been shown to be a limitation in production for previous NADPH oxidases. All of the previously discovered NADPH oxidases have shown to have a cysteine residue that is catalytically active. This thiol is oxidized to sulfenic acid and reduced back to the thiol as a part of the NADPH reduction mechanism. Studies have also shown that during this redox cycle the cysteine can also be overoxidized, producing a sulfinic or sulfonic acid, killing the enzymatic activity. This has been overcome to some extent by using reducing agents such as dithiothreitol (DTT) and β-mercaptoethanol. These reducing agents have shown to prevent overoxidation, thus elongating the catalytically active enzyme lifetime.

As demonstrated in this Example, NADH oxidase from *Lactobacillus plantarum* V is different in that it has a higher productivity indicated by its total turnover number (TTN) and is more stable against overoxidation as compared to its predecessors. While the native enzyme only showed activity on NADH, mutations in the substrate binding pocket were introduced to change its specificity and to accommodate NADPH.

Materials and Methods

Cloning and Site-Directed Mutagenesis.

The gene encoding NADH oxidase from *Lactobacillus plantarum* V was cloned out from the original plasmid through PCR using the following primers: forward primer (SEQ ID NO: 19) (5'-TGCATGCATGCCATGGTTAT-GAAAGTTATTGTAATTGGTTGTACCCA-3') and reverse primer (SEQ ID NO: 20) (5'-CCGCCGCCGCCG CTCGAGTTATTCAGTGACAGCTTCGGCC-3'). The PCR product was then gel purified with a Qiagen gel extraction kit and cloned into a pET-28a vector (Novagen, Inc.) using restriction sites NcoI and XhoI. The plasmid was then transformed into BL21(DE3)pLysS for expression.

Single and double mutations were performed on residues G178 and L179 into K, R and K, R, H respectively, through overlap and quikchange PCR using the following forward primers and their complementary reverse primers; G178K/R (SEQ ID NO: 21) (5'-GCAAGGTAAGGAAGTCACAC-TAATTGATARRTTACCACGGATTTTAAATAAATACT TAGACAA-3'), L179H/R (SEQ ID NO: 22) (5'-AGGTAAG-GAAGTCACACTAATTGATGGT CRYCCACGGATTTTAAATAAATACTTAGACAAAG-3'), L179K (SEQ ID NO: 23) (5'-AGGTAAGGAAGTCACAC-TAATTGATGGT AAACCACGGATTTTAAATAAATACTTAG ACAAA-3'), G178K/R/L179R/H (SEQ ID NO: 24) (5'-GCAAGGTAAG-GAAGTCACACTAATTGAT ARRCRYCCACGGATTTTAAATAAATACT TAGA-CAAAG-3'), G178K/R/L179K (SEQ ID NO: 25) (5'-GCAAGGTAAGGAAGTCACACTAATTGAT ARRAAACCACGGATTTTAAATAAATACT TAGA-CAAA-3'). Degenerate codons for K/R and H/R were used as ARR and CRY respectively.

Overexpression.

Growth and overexpression was carried out in MagicMedia™ *E. coli* Expression Medium (Invitrogen) with a final concentration of 30 μg. mL$^{-1}$ of kanamycin and chloromphenicol. A dual temperature protocol was used for growth, starting out at 30° C. for 6 hours, and then continued at room temperature for an additional 22 hours. Cultures were harvested by centrifugation in a Beckman centrifuge with a JS-5.2 rotor at 4000 rpm for 20 minutes in 50 mL conical tubes. The resulting cell pellet was either frozen, and stored at −80° C. or purified directly.

Enzyme Assay and Protein Determination.

Standard assays were performed at 25° C. in 100 mM TEA buffer (pH 7.5) with 5 mM DTT in cuvettes with either a 1 cm or 1 mm path length, depending on the concentration of substrate. Initial activity was measured by following the absorbance change using a Beckman Coulter DU 800 UV/Vis spectrophotometer at 340 nm. Activity of the enzyme was calculated using an extinction coefficient of NAD(P)H, ϵ, as 6.22 mM$^{-1}$ cm$^{-1}$. Unless otherwise noted, a substrate concentration of 0.2 mM NADPH was used for assays. 1 unit (U) of activity is defined as 1 mol min$^{-1}$.

The protein concentration was determined by a Bradford assay. BSA was used as standards, and the absorbance was measured on a biophotometer. SDS-page analysis was performed to determine to purity.

Purification.

Purification of NOX5 was carried out at 4° C. or on ice to prevent denaturation of the enzyme. Cell pellets were resuspended in 15 mL of 10 mM Tris-HCl buffer (pH 7.5) with 5 mM DTT (Buffer A) and sonicated at 14 watts for 30 seconds nine times in an ice water bath. Sonicated cells were centrifuged at 15000 rpm in a Beckman J2-21 with a JA-21 rotor for 30 minutes. The clarified cell lysate was transferred to a dialysis membrane and dialyzed against 250 mL of Buffer A with 50% ammonium sulfate for 2 hours. The dialysis membrane was then transferred to fresh buffer and further dialyzed for 2 hours. The solution was then centrifuged at 15000 rpm for 30 minutes. The resulting supernatant was filtered through a 0.8 µM filter and 0.2 µM filter in series. The filtrate was loaded onto a HIPREP™ 16/10 Butyl column on an AKTA. A reverse gradient separation was performed starting from Buffer A with 30% ammonium sulfate to 15%. The fractions with the highest activity were collected and dialyzed against a Buffer A for 2 hours. After exchanging the fresh buffer, the sample was dialyzed for an additional 2 hours. The sample was loaded on a HIPREP™ 16/10 DEAE anionic exchange column on the AKTA. Separation was achieved with Buffer A containing NaCl, a gradient of 150 mM to 250 mM. The resulting fractions were assayed, and the fractions with highest activity were collected as pure protein. The purified protein was either stored in 4° C. or in −20° C. with 25% glycerol.

pH Activity.

Enzyme pH activity profiles were obtained at 25° C. using 100 mM buffers with the following salts: sodium citrate from pH 4.0 to pH 6.5; sodium phosphate from pH 6.0 to pH 8.0; TEA from pH 7.0 to pH 8.0; Tris-HCl from pH 7.0 to pH 9.0; glycine from pH 9.0 to pH 10.0.

Temperature Activity.

Temperature dependent activity was studied by incubating the enzyme at different temperatures. After one minute of incubation, the standard assay was carried out. A temperature range of 10 to 55° C. was chosen for this study.

Temperature Stability.

Temperature stability was studied by incubating the enzyme at various temperatures for 30 minutes. The enzyme solution was then cooled down and assayed at 25° C. This study covered a temperature range of 15° C. to 55° C.

Kinetic Parameters.

Depending on the enzyme, a substrate concentration range from 1.5 µM up to 984 µM was investigated to determine the $k_{cat}$ and $K_M$ of NADPH. This was conducted with an excess of oxygen present in the system. The reaction was initiated by mixing two separate 2× solutions of each the substrate and enzyme. The specific activity was measured, and the kinetic parameters were calculated from that data.

Inhibition effects of $NAD^+$ and $H_2O_2$ were measured by incubating the enzyme with possible inhibitors for 30 minutes before the assay. For $NAD^+$, 0.2, 0.3, 0.4 and 0.6 mM were chosen and for $H_2O_2$, 25, 50, 100 and 200 µM were investigated.

Amplex Red Assay.

An Amplex Red Hydrogen Peroxide/Peroxidase Assay Kit (Invitrogen) was used to determine the amount of hydrogen peroxide ($H_2O_2$) produced during turnover. Various amounts of substrates were reacted and assayed to detect the presence of $H_2O_2$. The reactions were carried out in the provided 50 mM sodium phosphate buffer (pH 7.4). Standards for the calibration curve were made with the same reaction buffer.

Total Turnover Number (TTN).

Standard kinetic assays were performed with small amounts of enzyme. Assays were carried out for two to three hours until there was no more enzymatic conversion of the substrate.

Results and Discussion

NADH oxidase V from *Lactobacillus plantarum* (NOX5) consists of 1350 bp and has a predicted size of 49 kDa. Sequencing of the gene (SEQ ID NO. 1) showed a nucleotide mutation of C to T at position 45, but the resulting amino acid sequence (SEQ ID NO. 2) was the same as the predicted sequence.

Purification of NOX5 resulted in a yield of 14% of the total units and a 12.7 fold increase of specific activity. Purified NOX 5 shows a strong band at 49 kDa in SDS-page analysis. Table 1 is a table of purification. "Lysate" refers to clarified lysate; "AS50 dia." refers to the supernatant from centrifuged sample dialyzed against 50% ammonium sulfate; "Butyl dia." refers to the fractions collected from HIPREP™ 16/10 Butyl column dialyzed against 100 mM TEA pH 7.5 and 5 mM DTT; and "DEAE" refers to fractions collected from HIPREP™ 16/10 DEAE column.

TABLE 1

|  | Volume (ml) | Units (U) | Protein (mg) | Sp. ac. (U mg$^{-1}$) | Purification Fold | Yield (%) |
|---|---|---|---|---|---|---|
| Lysate | 20 | 1843.5 | 139.3 | 13.24 | 1.0 | 100 |
| AS50 dia. | 7 | 930.0 | 88.5 | 10.51 | 0.8 | 50 |
| Butyl dia. | 37.5 | 379.3 | 4.7 | 80.72 | 6.1 | 21 |
| DEAE | 20 | 261.9 | 1.6 | 167.5 | 12.7 | 14 |

Enzyme Activity and Stability.

NADPH oxidases will mostly be used in cofactor regeneration, as water and hydrogen peroxide are not of great interest for final products. As the true value of these enzymes are shown when they are coupled with other enzymes, the study of reaction conditions, especially in terms of pH and temperature, were necessary to maximize activity and stability.

Figure 2:
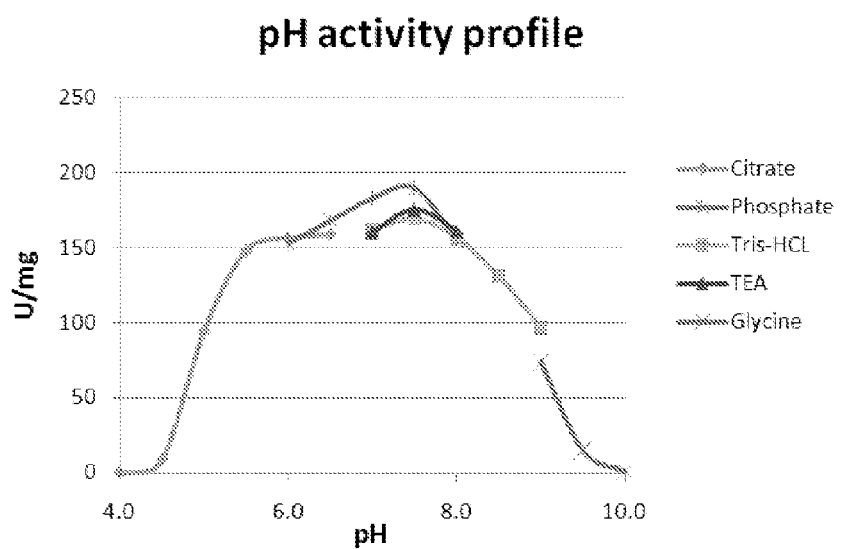
FIG. 2 illustrates the activity profile of NADH oxidase from *Lactobacillus plantarum* V (NOX5) at different pHs.

NOX5 showed a rather broad pH activity range. Maximum activity was found at pH 7.5, but the enzyme was fairly active from pH 5.5 to 8.0. (FIG. 2). This is a range that is common for many NADPH oxidases. The upper limit is also compatible with dehydrogenases that are active in alkaline conditions. Although it would be difficult to have a single corresponding maximum for both enzymes, a person of ordinary skill in the art could identify optimal conditions for a dehydrogenase and NOX5.

Figure 3:
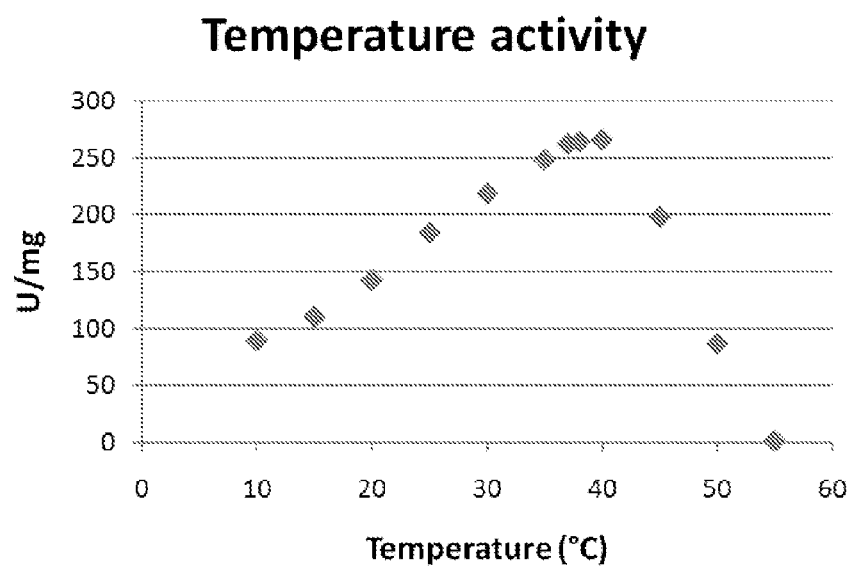
FIG. 3 illustrates the activity profile of NOX5 at various temperatures.
Figure 4:
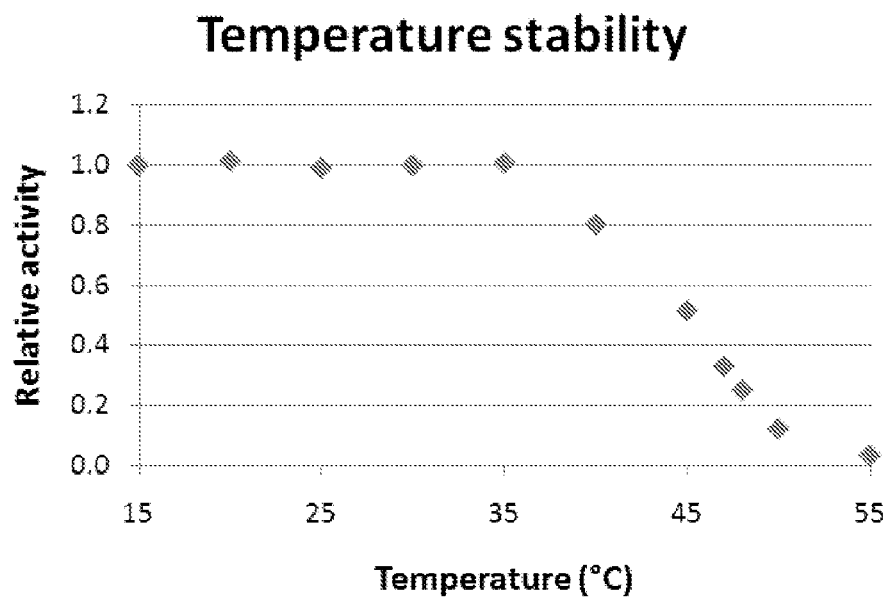
FIG. 4 is a $T_{50}^{30}$ plot that demonstrates stability of NOX5 by incubating at different temperatures.

The temperature activity profile showed that maximum instantaneous activity was found at 40° C., and the activity quickly reached zero beyond that. (FIGS. 3 and 4). Using an Arrhenius model, the activation energy, $E_a$, was calculated as 32.7 kJ mol$^{-1}$, and the deactivation energy, $E_d$, was calculated as −93.6 kJ mol$^{-1}$. The temperature that exhibited half of the original activity, $T_{50}^{30}$, was estimated to be 45° C. At 55° C., the enzyme was inactive. Enthalpy of deactivation, ΔH, was calculated to be 4.98 kJ·mol$^{-1}$.

Kinetic Parameters.

Figure 5:
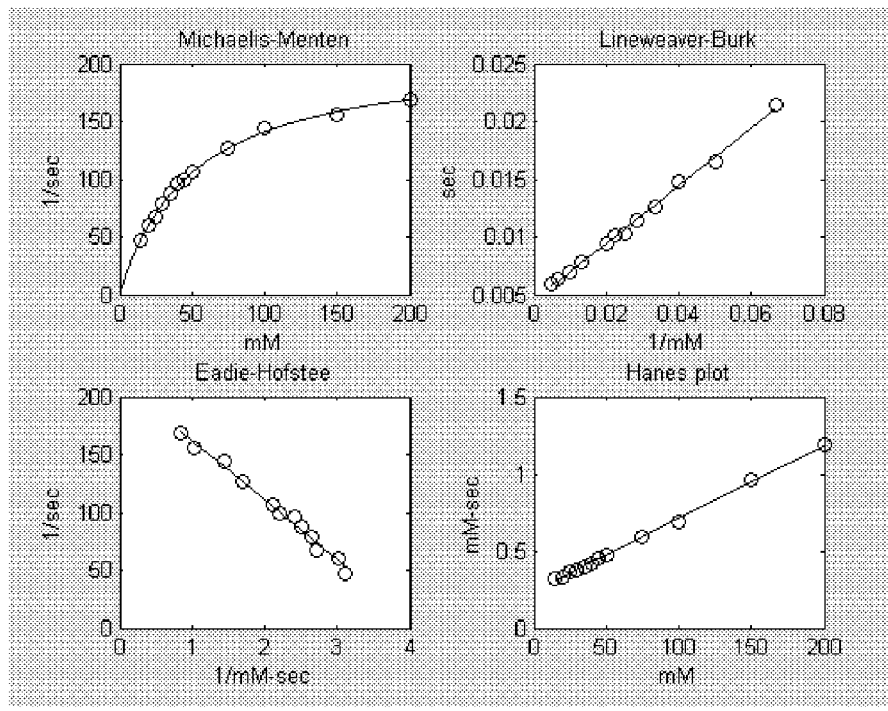
FIG. 5 is a plot of kinetics using different models: non-linear Michaelis-Menten, Lineweaver-Burk, Eadie-Hofstee, and Hanes-Woolf.

The data was fitted with four different models: non-linear Michaelis-Menten, Lineweaver-Burk, Eadie-Hofstee and Hanes. Through non-linear fitting, $k_{cat}$ and $K_M$ of the wild type were measured to be 211.6 s$^{-1}$ and 50.2 µM, respectively with an $R^2$ of 0.998. (FIG. 5).

Figure 6:
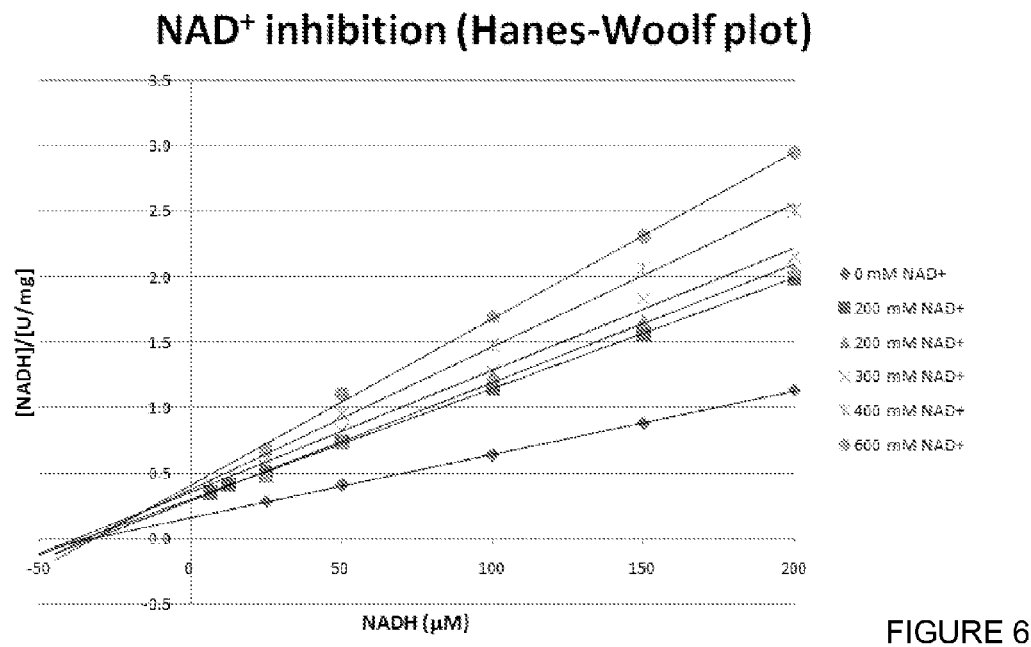
FIG. 6 graphically depicts a Hanes-Woolf plot of NAD$^+$ inhibition pattern of NOX5.

Possible product inhibitory effects were investigated by incubating the enzyme with different concentrations of $NAD^+$. $NAD^+$ exhibited a non-competitive inhibition pattern where the $U_{max}$ mg$^{-1}$ decreased as the inhibitor concentration increased while $K_{M,app}$ was consistent. Analysis of the different concentrations showed that the $K_I$ of $NAD^+$ was 289 µM. (FIG. 6).

To determine whether NOX5 is a water or hydrogen peroxide producing enzyme, an amplex red assay was performed. The presence of $H_2O_2$ can be confirmed by incubating the standard assay mixture with amplex red and peroxidase. Produced resorufin can be detected using a fluorescence spectroscopy analysis. NOX5 produced $H_2O_2$ at a 2.63% ratio of NADH strongly suggesting that it is a water forming NADPH oxidase.

Total Turnover Number (TTN).

Total turnover number (TTN) is a measurement of catalyst productivity. For biocatalysts, TTN is defined as the total amount of product produced over the lifetime of an enzyme. Calculations of TTN were performed by dividing the change of NADPH concentration by the amount of enzyme that was used for each assay. In the standard assay conditions with the presence of DTT the TTN was found to be about 168,000, consistently, at 25° C. (data not shown).

This experiment was repeated to see if the presence of reducing agents had any effect on the total turnover number. The stock solution of enzyme was dialyzed against 250 mL of 10 mM Tris-HCl (pH 7.5) for two hours. The solution was then exchanged and dialyzed for an additional 2 hours. The TTN was then measured with the dialyzed enzyme with and without reducing agents. DTT and β-mercaptoethanol (β-ME) were used at a concentration of 5 mM. The TTN for the sample with no reducing agents, DTT and β-ME were 128,000, 168,000 and 107,000, respectively. The presence of DTT had a positive effect, but it was not as dramatic compared to the NADH oxidase from *Lactobacillus sanfranciscensis*. β-ME did not have a positive effect at all and actually decreased the TTN.

To examine TTN limitation possibilities, three properties were investigated: i) thermal stability of enzyme at 25° C.; ii) presence of hydrogen peroxide ($H_2O_2$) and stability of enzyme against it; and iii) product ($NAD^+$) inhibition in the system.

Thermal stability at 25° C. was measured by incubating the enzyme for extended periods of time. The enzyme was then assayed to check the remaining activity (data not shown). The thermal stability at 25° C. was investigated in order to show the relevance of thermal degradation during turnover. Through this study, it can be concluded that the enzyme shows to be inactive before it is thermally deactivated.

The effect of $H_2O_2$ was studied with a concentration range up to 200 μM, which would be the total amount produced from a standard assay if the enzyme was a hydrogen peroxide producing NADPH oxidase. Even at high concentrations, there was no change found in the initial specific activity (data not shown), thus showing that the enzyme is indeed quite stable against $H_2O_2$.

The presence of $NAD^+$ inhibition, and its pattern was known. However, even at high concentrations of $NAD^+$, there was a reasonable amount of activity. So, it would be difficult to conclude that NAD+ had inhibited the reaction completely.

Example 2

Mutation of NADH Oxidase from *Lactobacillus plantarum* for NADPH Activity

Since the wild type NOX5 had activity exclusively towards NADH, and had little to no activity towards NADPH, mutational options were investigated to introduce NADPH activity. Crystal structure comparisons of NADPH oxidase from *Lactobacillus sanfranciscensis* and a homology model of NOX5 from *Lactobacillus plantarum* showed differences in where the 2′-phosphate would be located. The one from *L. sanfranciscensis* had a histidine, which would be able to accommodate the negative charge but NOX5 only had hydrophobic residues in that area. Based on this knowledge, different basic residues were chosen for mutation in that region.

Single mutations were done on residues G178 and L179 into K, R and K, R, H respectively, and double mutations were also investigated with different combinations of the single mutations. The mutation of G178H was excluded due to the fact that the enzyme would then have two histidines next to each other, creating steric hindrance in the binding pocket. The resulting mutants were expressed on small scale and assayed at the cell lysate level. Table 2 provides the NOX5 mutants and the activity of the mutants at the cell lysate level.

Among the mutants, L179R retained the highest amount of NADH activity, and G178R/L179R had the highest activity for NADPH. Although not wishing to be bound by any particular theory, it is believed that a positive charge is introduced through the mutation at L179R, and the additional mutation at G178R stabilizes the positioning, effectively decreasing the amount of free rotation of L179R through hydrogen bonding. It seems reasonable for arginine to have the largest effect, as it has the most options for hydrogen bonding. The low activity of L179H can be explained by the presence of an adjacent proline causing steric hindrance.

TABLE 2

| Mutant | NADH activity (U/mg) | NADPH activity (U/mg) |
| --- | --- | --- |
| Wild Type | 10.0 | 0.00 |
| G178K | 3.92 | 0.46 |
| G178R | 1.51 | 0.23 |
| L179K | 5.14 | 1.03 |
| L179R | 7.32 | 1.76 |
| L179H | 1.37 | 0.64 |
| G178K/L179K | 0.84 | 3.11 |
| G178K/L179R | 2.00 | 5.68 |
| G178K/L179H | 1.24 | 3.85 |
| G178R/L179K | 0.94 | 3.56 |
| G178R/L179R | 2.64 | 6.00 |
| G178R/L179H | 0.64 | 0.52 |

Study of mutants L179R and G178R/L179R. L179R and G178R/L179R were selected for further purification. Table 3 provides kinetic parameters of wild-type (WT) and mutant NADPH oxidases. L179R was not as active as the wild-type having a $k_{cat, NADH}$ of 122.0 $s^{-1}$. However, the $K_{M, NADH}$ was much lower at 6.56 μM, improving the $k_{cat}/K_M$ by more than 4-fold. The mutant also showed NADPH activity but had a very high $K_M$ of 489.6 μM. The double mutant G178R/L179R also had the same trend for NADH as L179R but to a larger extent. The $k_{cat, NADH}$ was 34.0 $s^{-1}$ and the $K_{M, NADH}$ was 34.0 μM, resulting in a $k_{cat}/K_M$ of 13.2 $μM^{-1} s^{-1}$. It also showed a $k_{cat}/K_M$ for NADPH at 11.7 $μM^{-1} s^{-1}$, where at, NADPH was 114.1 $s^{-1}$ and the $K_{M, NADPH}$ was 9.76 μM. Overall, both enzymes were improvements over the wild-type, in terms of $k_{cat}/K_M$.

TABLE 3

| | NADH | | | NADPH | | |
| --- | --- | --- | --- | --- | --- | --- |
| enzyme | $k_{cat}$ ($s^{-1}$) | $K_M$ (μM) | $k_{cat}/K_M$ ($μM^{-1} \cdot s^{-1}$) | $k_{cat}$ ($s^{-1}$) | $K_M$ (μM) | $k_{cat}/K_M$ ($μM^{-1} \cdot s^{-1}$) |
| WT | 211.6 | 50.2 | 4.22 | — | — | — |
| L179R | 122.0 | 6.56 | 18.6 | 146.4 | 489.6 | 0.30 |
| G178R/L179R | 34.0 | 2.57 | 13.2 | 114.1 | 9.76 | 11.7 |

The TTN of the mutants were measured and the same trend, where the presence of reducing agents did not affect the enzyme to a great extent, was found. The double mutant successfully exhibited NADPH activity, expanding the range of applications where this enzyme could be used.

Example 3

Higher Operational Stability of *Lactobacillus plantarum* NAD(P)H Oxidase (Higher Total Turnover Number)

Comparison of NADPH oxidases. Table 4 provides a comparison of TTN with and without DTT, for NADH oxidases from *L. plantarum, Lactobacillus sanfranciscensis, Lactococcus lactis.*

TABLE 4

| organism | enzyme | NADH TTN | NADH TTN with DTT | NADPH TTN | NADPH TTN with DTT |
|---|---|---|---|---|---|
| *L. plantarum* | NOX5 WT | 128,000 | 168,000 | — | — |
|  | L179R | 181,000 | 149,000 |  |  |
|  | G178R/ L179R | 108,000 | 128,000 | 105,000 | 118,000 |
| *L. sanfranciscensis* | NOX2 | 5,000 | 112,500 |  |  |
| *L. lactis* | NOX2 | 38,740 | 78,480 | — | — |

NOX5 has shown a higher total turnover number with and even without any reducing agents. This is an indication of improved stability against overoxidation at the catalytically active cysteine residue. Since there are known effects of inhibition of DTT on certain rare sugar producing dehydrogenases, such as mannitol dehydrogenase from *Apium graveolens*, it is preferable for an NADPH oxidase to be is stable without DTT. Also, improved stability without reducing agents would be a advantage in the pharmaceutical industry (or any other area that is related for the matter) where the presence of these reducing agents lack acceptability.

A broad study of NOX5 from *Lactobacillus plantarum* was conducted to study the possibility of an NADPH oxidase stable against overoxidation. In this study, pH and temperature characteristics were investigated to identify a common ground for enzyme coupled systems. Kinetic parameters were defined and the TTN was studied to discover the advantages compared to previous NADPH oxidases. Through this study, the high stability of this enzyme was proven with and without the presence of reducing agents.

As the wild-type enzyme demonstrates specificity for a NADH substrate, in order to be able to utilize NADPH, mutations were made to change the specificity of the enzyme. By positioning different positively charged residues to interact and accommodate the 2'-phosphate of NADPH, it was possible to find a mutation that would be of this effect. This will broaden the range and usage of this NADPH oxidase, that has higher stability against over oxidation than its predecessors.

SEQUENCE LISTING

SEQ ID NO: 1-NADH Oxidase Obtained from
*Lactobacillus plantarum*
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDGLPRILNKYLD
KEFTDRVEQDFVDHGIKMALNQMVQGFSDDGKEVTVKTDKGSYTADM
AILCVGPRPNTGLLKGKVDMNANGSIKTNDYMQTSDPDIYGAGDSVA
VHYNPTKKDAYIPLATNAVRQGTLVGLNIFKPTRKYMGTQSTSGLML
FGGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 2-NADH Oxidase Obtained from
*Lactobacillus plantarum*
ATGAAAGTTATTGTAATTGGTTGTACCCATGCCGGCACTGCTGCTGT
TAATCAGATTTTAGCATCAAATCCAGATACTGAAGTGACGATTTATG
AAAGAAATGACAATGTCTCGTTCCTATCCTGTGGGATCGCACTTTAC
CTTGGCGGCCAAGTTGCTGATCCTCAAGGCCTATTTTATTCCAGTCC
TGAACAGTTAGCTAAGTTAGGCGCAACTGTTCATATGCAACATGATG
TGACGGATGTGAATACTGACAAACATGAAATTACGGTTACTGACTTA
AAGACTGGTGAATCTAAGACTGATCACTATGACAAGTTAGTTGTCAC
TACTGGTTCATGGCCTGTTATTCCACCAATTGACGGCATCGATAGTC
CCAATGTCTACTTATGCAAGAACTGGACGCACGCTCAGAATTTATGG
GAAGCAGCCAAACCAGCTAAGCGGGTCATTGTGATCGGTGGCGGTTA
TATCGGTACTGAATTAGTTGAAGCTTACCAGAAGCAAGGTAAGGAAG
TCACACTAATTGATGGTTTACCACGGATTTTAAATAAATACTTAGAC
AAAGAATTCACTGACCGGGTTGAACAAGACTTTGTTGATCACGGTAT
CAAGATGGCTTTGAATCAAATGGTGCAAGGCTTCAGTGATGATGGTA
AAGAAGTTACGGTCAAGACTGACAAGGGCAGCTACACAGCCGACATG
GCGATTCTTTGTGTTGGCTTCCGGCCAAATACCGGCTTACTCAAGGG
CAAGGTCGATATGAACGCTAATGGCTCGATCAAGACCAATGACTACA
TGCAAACTTCTGATCCAGACATTTACGGGGCTGGTGACTCGGTTGCT
GTTCACTATAACCCAACTAAGAAAGATGCTTATATCCCATTAGCAAC
GAATGCGGTTCGCCAAGGAACCTTAGTTGGTTTGAACATCTTCAAGC
CAACGCGGAAGTACATGGGGACACAATCAACTTCTGGGTTAATGTTG
TTCGGCCAAACCATCGTTTCATCTGGGATGACCCTAGAACATGCACA
GGCCGAAAATGTTCCGGCAGCCGCTGTCACTTTTGAAGACAACTACC
GGCCAGAATTTATGCCAACCACTAAGCCTGTTTTAATGCAATTGGTT
TACAATCCTGAAACTCGCGAAATCCTAGGTGCACAATTCATGAGTGA
ACATGATGTTTCGCAATCAGCCAATGTGATTTCAGTGATGATTCAAA
ATCACAATACCATTGACGACTTAGGGTTCGTAGATATGTTCTTCCAA
CCAATTTACGACCGGCCATTTAACTATTTGAACTTACTTGGTCAAGC
AGCGATTGCCCATGCGGCCGAAGCTGTCACTGAATAA SEQ ID NO: 3-NADH Oxidase Derived from
*Lactobacillus plantarum*, G178K mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDKLPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 4-NADH Oxidase Derived from
*Lactobacillus plantarum*, G178R mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDRLPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 5-NADH Oxidase Derived from
*Lactobacillus plantarum*, G178K/R mutants
ATGAAAGTTATTGTAATTGGTTGTACCCATGCCGGCACTGCTGCTGT
TAATCAGATTTTAGCATCAAATCCAGATACTGAAGTGACGATTTATG
AAAGAAATGACAATGTCTCGTTCCTATCCTGTGGGATCGCACTTTAC
CTTGGCGGCCAAGTTGCTGATCCTCAAGGCCTATTTTATTCCAGTCC
TGAACAGTTAGCTAAGTTAGGCGCAACTGTTCATATGCAACATGATG
TGACGGATGTGAATACTGACAAACATGAAATTACGGTTACTGACTTA
AAGACTGGTGAATCTAAGACTGATCACTATGACAAGTTAGTTGTCAC
TACTGGTTCATGGCCTGTTATTCCACCAATTGACGGCATCGATAGTC
CCAATGTCTACTTATGCAAGAACTGGACGCACGCTCAGAATTTATGG
GAAGCAGCCAAACCAGCTAAGCGGGTCATTGTGATCGGTGGCGGTTA
TATCGGTACTGAATTAGTTGAAGCTTACCAGAAGCAAGGTAAGGAAG
TCACACTAATTGATARRTTACCACGGATTTTAAATAAATACTTAGAC

```
AAAGAATTCACTGACCGGGTTGAACAAGACTTTGTTGATCACGGTAT
CAAGATGGCTTTGAATCAAATGGTGCAAGGCTTCAGTGATGATGGTA
AAGAAGTTACGGTCAAGACTGACAAGGGCAGCTACACAGCCGACATG
GCGATTCTTTGTGTTGGCTTCCGGCCAAATACCGGCTTACTCAAGGG
CAAGGTCGATATGAACGCTAATGGCTCGATCAAGACCAATGACTACA
TGCAAACTTCTGATCCAGACATTTACGGGGCTGGTGACTCGGTTGCT
GTTCACTATAACCCAACTAAGAAAGATGCTTATATCCCATTAGCAAC
GAATGCCGGTTCGCCAAGGAACCTTAGTTGGTTTGAACATCTTCAAGC
CAACGCGGAAGTACATGGGGACACAATCAACTTCTGGGTTAATGTTG
TTCGGCCAAACCATCGTTTCATCTGGGATGACCCTAGAACATGCACA
GGCCGAAAATGTTCCGGCAGCCGCTGTCACTTTTGAAGACAACTACC
GGCCAGAATTTATGCCAACCACTAAGCCTGTTTTAATGCAATTGGTT
TACAATCCTGAAACTCGCGAAATCCTAGGTGCACAATTCATGAGTGA
ACATGATGTTTCGCAATCAGCCAATGTGATTTCAGTGATGATTCAAA
ATCACAATACCATTGACGACTTAGGGTTCGTAGATATGTTCTTCCAA
CCAATTTACGACCGGCCATTTAACTATTTGAACTTACTTGGTCAAGC
AGCGATTGCCCATGCGGCCGAAGCTGTCACTGAATAA

SEQ ID NO: 6-NADH Oxidase Derived from
Lactobacillus plantarum, L179K mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDGKPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 7-NADH Oxidase Derived from
Lactobacillus plantarum, L179K mutant
ATGAAAGTTATTGTAATTGGTTGTACCCATGCCGGCACTGCTGCTGT
TAATCAGATTTAGCATCAAATCCAGATACTGAAGTGACGATTTATG
AAAGAAATGACAATGTCTCGTTCCTATCCTGTGGGATCGCACTTTAC
CTTGGCGGCCAAGTTGCTGATCCTCAAGGCCTATTTTATTCCAGTCC
TGAACAGTTAGCTAAGTTAGGCGCAACTGTTCATATGCAACATGATG
TGACGGATGTGAATACTGACAAACATGAAATTACGGTTACTGACTTA
AAGACTGGTAATCTAAGACTGATCACTATGACAAGTTAGTTGTCAC
TACTGGTTCATGGCCTGTTATTCCACCAATTGACGGCATCGATAGTC
CCAATGTCTACTTATGCAAGAACTGGACGCACGCTCAGAATTTATGG
GAAGCAGCCAAACCAGCTAAGCGGGTCATTGTGATCGGTGGCGGTTA
TATCGGTACTGAATTAGTTGAAGCTTACCAGAAGCAAGGTAAGGAAG
TCACACTAATTGATGGTAAACACGGATTTTAAATAAATACTTAGAC
AAAGAATTCACTGACCGGGTTGAACAAGACTTTGTTGATCACGGTAT
CAAGATGGCTTTGAATCAAATGGTGCAAGGCTTCAGTGATGATGGTA
AAGAAGTTACGGTCAAGACTGACAAGGGCAGCTACACAGCCGACATG
GCGATTCTTTGTGTTGGCTTCCGGCCAAATACCGGCTTACTCAAGGG
CAAGGTCGATATGAACGCTAATGGCTCGATCAAGACCAATGACTACA
TGCAAACTTCTGATCCAGACATTTACGGGGCTGGTGACTCGGTTGCT
GTTCACTATAACCCAACTAAGAAAGATGCTTATATCCCATTAGCAAC
GAATGCCGGTTCGCCAAGGAACCTTAGTTGGTTTGAACATCTTCAAGC
CAACGCGGAAGTACATGGGGACACAATCAACTTCTGGGTTAATGTTG
TTCGGCCAAACCATCGTTTCATCTGGGATGACCCTAGAACATGCACA
GGCCGAAAATGTTCCGGCAGCCGCTGTCACTTTTGAAGACAACTACC
GGCCAGAATTTATGCCAACCACTAAGCCTGTTTTAATGCAATTGGTT
TACAATCCTGAAACTCGCGAAATCCTAGGTGCACAATTCATGAGTGA
ACATGATGTTTCGCAATCAGCCAATGTGATTTCAGTGATGATTCAAA
ATCACAATACCATTGACGACTTAGGGTTCGTAGATATGTTCTTCCAA
CCAATTTACGACCGGCCATTTAACTATTTGAACTTACTTGGTCAAGC
AGCGATTGCCCATGCGGCCGAAGCTGTCACTGAATAA SEQ ID NO: 8-NADH Oxidase Derived from
Lactobacillus plantarum, L179R mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDRKPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 9-NADH Oxidase Derived from
Lactobacillus plantarum, L179H mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDGHPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 10-NADH Oxidase Derived from
Lactobacillus plantarum, L179H/R mutants
ATGAAAGTTATTGTAATTGGTTGTACCCATGCCGGCACTGCTGCTGT
TAATCAGATTTAGCATCAAATCCAGATACTGAAGTGACGATTTATG
AAAGAAATGACAATGTCTCGTTCCTATCCTGTGGGATCGCACTTTAC
CTTGGCGGCCAAGTTGCTGATCCTCAAGGCCTATTTTATTCCAGTCC
TGAACAGTTAGCTAAGTTAGGCGCAACTGTTCATATGCAACATGATG
TGACGGATGTGAATACTGACAAACATGAAATTACGGTTACTGACTTA
AAGACTGGTGAATCTAAGACTGATCACTATGACAAGTTAGTTGTCAC
TACTGGTTCATGGCCTGTTATTCCACCAATTGACGGCATCGATAGTC
CCAATGTCTACTTATGCAAGAACTGGACGCACGCTCAGAATTTATGG
GAAGCAGCCAAACCAGCTAAGCGGGTCATTGTGATCGGTGGCGGTTA
TATCGGTACTGAATTAGTTGAAGCTTACCAGAAGCAAGGTAAGGAAG
TCACACTAATTGATGGTCYRCCACGGATTTTAAATAAATACTTAGAC
AAAGAATTCACTGACCGGGTTGAACAAGACTTTGTTGATCACGGTAT
CAAGATGGCTTTGAATCAAATGGTGCAAGGCTTCAGTGATGATGGTA
AAGAAGTTACGGTCAAGACTGACAAGGGCAGCTACACAGCCGACATG
GCGATTCTTTGTGTTGGCTTCCGGCCAAATACCGGCTTACTCAAGGG
CAAGGTCGATATGAACGCTAATGGCTCGATCAAGACCAATGACTACA
TGCAAACTTCTGATCCAGACATTTACGGGCTGGTGACTCGGTTGCT
GTTCACTATAACCCAACTAAGAAAGATGCTTATATCCCATTAGCAAC
GAATGCCGGTTCGCCAAGGAACCTTAGTTGGTTTGAACATCTTCAAGC
CAACGCGGAAGTACATGGGGACACAATCAACTTCTGGGTTAATGTTG
TTCGGCCAAACCATCGTTTCATCTGGGATGACCCTAGAACATGCACA
GGCCGAAAATGTTCCGGCAGCCGCTGTCACTTTTGAAGACAACTACC
GGCCAGAATTTATGCCAACCACTAAGCCTGTTTTAATGCAATTGGTT
TACAATCCTGAAACTCGCGAAATCCTAGGTGCACAATTCATGAGTGA
ACATGATGTTTCGCAATCAGCCAATGTGATTTCAGTGATGATTCAAA
ATCACAATACCATTGACGACTTAGGGTTCGTAGATATGTTCTTCCAA
CCAATTTACGACCGGCCATTTAACTATTTGAACTTACTTGGTCAAGC
AGCGATTGCCCATGCGGCCGAAGCTGTCACTGAATAA SEQ ID NO: 11-NADH Oxidase Derived from
Lactobacillus plantarum, G178K/L179K mutants
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDKKPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 12-NADH Oxidase Derived from
Lactobacillus plantarum, G178R/L179K mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDRKPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 13-NADH Oxidase Derived from
Lactobacillus plantarum G178R/K/L179K mutants
ATGAAAGTTATTGTAATTGGTTGTACCCATGCCGGCACTGCTGCTGT
TAATCAGATTTAGCATCAAATCCAGATACTGAAGTGACGATTTATG
AAAGAAATGACAATGTCTCGTTCCTATCCTGTGGGATCGCACTTTAC
CTTGGCGGCCAAGTTGCTGATCCTCAAGGCCTATTTTATTCCAGTCC
```

SEQUENCE LISTING

```
TGAACAGTTAGCTAAGTTAGGCGCAACTGTTCATATGCAACATGATG
TGACGGATGTGAATACTGACAAACATGAAATTACGGTTACTGACTTA
AAGACTGGTGAATCTAAGACTGATCACTATGACAAGTTAGTTGTCAC
TACTGGTTCATGGCCTGTTATTCCACCAATTGACGGCATCGATAGTC
CCAATGTCTACTTATGCAAGAACTGGACGCACGCTCAGAATTTATGG
GAAGCAGCCAAACCAGCTAAGCGGGTCATTGTGATCGGTGGCGGTTA
TATCGGTACTGAATTAGTTGAAGCTTACCAGAAGCAAGGTAAGGAAG
TCACACTAATTGATARRAAACCACGGATTTTAAATAAATACTTAGAC
AAAGAATTCACTGACCGGGTTGAACAAGACTTTGTTGATCACGGTAT
CAAGATGGCTTTGAATCAAATGGTGCAAGGCTTCAGTGATGATGGTA
AAGAAGTTACGGTCAAGACTGACAAGGGCAGCTACACAGCCGACATG
GCGATTCTTTGTGTTGGCTTCCGGCCAAATACCGGCTTACTCAAGGG
CAAGGTCGATATGAACGCTAATGGCTCGATCAAGACCAATGACTACA
TGCAAACTTCTGATCCAGACATTTACGGGGCTGGTGACTCGGTTGCT
GTTCACTATAACCCAACTAAGAAAGATGCTTATATCCCATTAGCAAC
GAATGCGGTTCGCCAAGGAACCTTAGTTGGTTTGAACATCTTCAAGC
CAACGCGGAAGTACATGGGGACACAATCAACTTCTGGGTTAATGTTG
TTCGGCCAAACCATCGTTTCATCTGGGATGACCCTAGAACATGCACA
GGCCGAAAATGTTCCGGCAGCCGCTGTCACTTTTGAAGACAACTACC
GGCCAGAATTTATGCCAACCACTAAGCCTGTTTTAATGCAATTGGTT
TACAATCCTGAAACTCGCGAAATCCTAGGTGCACAATTCATGAGTGA
ACATGATGTTTCGCAATCAGCCAATGTGATTTCAGTGATGATTCAAA
ATCACAATACCATTGACGACTTAGGGTTCGTAGATATGTTCTTCCAA
CCAATTTACGACCGGCCATTTAACTATTTGAACTTACTTGGTCAAGC
AGCGATTGCCCATGCGGCCGAAGCTGTCACTGAATAA
```

SEQ ID NO: 14-NADH Oxidase Derived from
Lactobacillus plantarum, G178K/L179R mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDKRPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 15-NADH Oxidase Derived from
Lactobacillus plantarum, G178K/L179H mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDKHPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEFMPTTKPVLMQLV
YNPETREILGAQFMSEHDVSQSANVISVMIQNHNTIDDLGFVDMFFQ
PIYDRPFNYLNLLGQAAIAHAAEAVTE SEQ ID NO: 16-NADH Oxidase Derived from
Lactobacillus plantarum, G178R/L179R mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDRRPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEEMPTTKPVLMQLV
YNPETREILGAQEMSEHDVSQSANVISVMIQNHNTIDDLGFVDMFFQ
PIYDRPFNYLNLLGQAAIAHAAEAVTE SEQ ID NO: 17-NADH Oxidase Derived from
Lactobacillus plantarum, G178R/L179H mutant
MKVIVIGCTHAGTAAVNQILASNPDTEVTIYERNDNVSFLSCGIALY
LGGQVADPQGLFYSSPEQLAKLGATVHMQHDVTDVNTDKHEITVTDL
KTGESKTDHYDKLVVTTGSWPVIPPIDGIDSPNVYLCKNWTHAQNLW
EAAKPAKRVIVIGGGYIGTELVEAYQKQGKEVTLIDRHPRILNKYLD
KEFTDRVEQDFVDHGIKMALNQMVQGFSDDGKEVTVKTDKGSYTADM
AILCVGFRPNTGLLKGKVDMNANGSIKTNDYMQTSDPDIYGAGDSVA
VHYNPTKKDAYIPLATNAVRQGTLVGLNIFKPTRKYMGTQSTSGLML
FGQTIVSSGMTLEHAQAENVPAAAVTFEDNYRPEEMPTTKPVLMQLV
YNPETREILGAQEMSEHDVSQSANVISVMIQNHNTIDDLGFVDMFFQ
PIYDRPFNYLNLLGQAAIAHAAEAVTE SEQ ID NO: 18-NADH Oxidase Derived from
Lactobacillus plantarum, G178K/R /L179R/H
mutants

```
ATGAAAGTTATTGTAATTGGTTGTACCCATGCCGGCACTGCTGCTGT
TAATCAGATTTTAGCATCAAATCCAGATACTGAAGTGACGATTTATG
AAAGAAATGACAATGTCTCGTTCCTATCCTGTGGGATCGCACTTTAC
CTTGGCGGCCAAGTTGCTGATCCTCAAGGCCTATTTTATTCCAGTCC
TGAACAGTTAGCTAAGTTAGGCGCAACTGTTCATATGCAACATGATG
TGACGGATGTGAATACTGACAAACATGAAATTACGGTTACTGACTTA
AAGACTGGTGAATCTAAGACTGATCACTATGACAAGTTAGTTGTCAC
TACTGGTTCATGGCCTGTTATTCCACCAATTGACGGCATCGATAGTC
CCAATGTCTACTTATGCAAGAACTGGACGCACGCTCAGAATTTATGG
GAAGCAGCCAAACCAGCTAAGCGGGTCATTGTGATCGGTGGCGGTTA
TATCGGTACTGAATTAGTTGAAGCTTACCAGAAGCAAGGTAAGGAAG
TCACACTAATTGATARRCRYCCACGGATTTTAAATAAATACTTAGAC
AAAGAATTCACTGACCGGGTTGAACAAGACTTTGTTGATCACGGTAT
CAAGATGGCTTTGAATCAAATGGTGCAAGGCTTCAGTGATGATGGTA
AAGAAGTTACGGTCAAGACTGACAAGGGCAGCTACACAGCCGACATG
GCGATTCTTTGTGTTGGCTTCCGGCCAAATACCGGCTTACTCAAGGG
CAAGGTCGATATGAACGCTAATGGCTCGATCAAGACCAATGACTACA
TGCAAACTTCTGATCCAGACATTTACGGGGCTGGTGACTCGGTTGCT
GTTCACTATAACCCAACTAAGAAAGATGCTTATATCCCATTAGCAAC
GAATGCGGTTCGCCAAGGAACCTTAGTTGGTTTGAACATCTTCAAGC
CAACGCGGAAGTACATGGGGACACAATCAACTTCTGGGTTAATGTTG
TTCGGCCAAACCATCGTTTCATCTGGGATGACCCTAGAACATGCACA
GGCCGAAAATGTTCCGGCAGCCGCTGTCACTTTTGAAGACAACTACC
GGCCAGAATTTATGCCAACCACTAAGCCTGTTTTAATGCAATTGGTT
TACAATCCTGAAACTCGCGAAATCCTAGGTGCACAATTCATGAGTGA
ACATGATGTTTCGCAATCAGCCAATGTGATTTCAGTGATGATTCAAA
ATCACAATACCATTGACGACTTAGGGTTCGTAGATATGTTCTTCCAA
CCAATTTACGACCGGCCATTTAACTATTTGAACTTACTTGGTCAAGC
AGCGATTGCCCATGCGGCCGAAGCTGTCACTGAATAA
```

SEQ ID NO: 19-Forward Cloning Primer for NADH
Oxidase from Lactobacillus plantarum
TGCATGCATGCCATGGTTATGAAAGTTATTGTAATTGGTTGTACCCA SEQ ID NO: 20-Reverse Cloning Primer for NADH
Oxidase from Lactobacillus plantarum
CCGCCGCCGCCGCTCGAGTTATTCAGTGACAGCTTCGGCC SEQ ID NO: 21-Forward Primer for NADH Oxidase
for Lactobacillus plantarum G178K/R mutants
GCAAGGTAAGGAAGTCACACTAATTGATARRTTACCACGGATTTTAA
ATAAATACTTAGACAA SEQ ID NO: 22-Forward Primer for NADH Oxidase
for Lactobacillus plantarum L179H/R mutants
AGGTAAGGAAGTCACACTAATTGATGGTCRYCCACGGATTTTAAATA
AATACTTAGACAAAG SEQ ID NO: 23-Forward Primer for NADH Oxidase
for Lactobacillus plantarum L179K mutant
AGGTAAGGAAGTCACACTAATTGATGGTAAACCACGGATTTTAAATA
AATACTTAGACAAA SEQ ID NO: 24-Forward Primer for NADH Oxidase
for Lactobacillus plantarum G178K/R/L179R/H
mutants
GCAAGGTAAGGAAGTCACACTAATTGATARRCRYCCACGGATTTTAA
ATAAATACTTAGACAAAG SEQ ID NO: 25-Forward Primer for NADH Oxidase
for Lactobacillus plantarum G178K/R/L179K
mutants
GCAAGGTAAGGAAGTCACACTAATTGATARRAAACCACGGATTTTAA
ATAAATACTTAGACAAA

REFERENCES

1. A. Zaks, "Industrial biocatalysis", Curr. Opin. Chem. Biol. 2001, 5, 130-136.
2. A. Liese and M. V. Filho, "Production of fine chemicals using biocatalysis", Curr. Opin. Biotechnol. 1999, 10, 595-603.

3. J. D. Rozzell, "Biocatalysis at commercial scale: Myths and realities", *Chimica Oggi* 1999, 42-47.
4. A. S. Bommarius, M. Schwarm and K. Drauz, "Comparison of Different Chemoenzymatic Process Routes to Enantiomerically Pure Amino Acids", *Chimia* 2001, 55, 50-59.
5. D. A. Evans, T. C. Britton, J. A. Ellman and R. L. Dorow, 1990, "The asymmetric synthesis of α-amino acids. Electrophilic azidation of chiral imide enolates, a practical approach to the synthesis of (R)- and (S)-α-azido carboxylic acids", *J. Am. Chem. Soc.,* 112, 4011-4030.
6. U. Groth, C. Schmeck and U. Schöllkopf, 1993, "Asymmetric synthesis of α-amino acid benzyl esters via the bisbenzyl bislactim ether of cyclo(-L-Val-Gly-)", *Liebigs Ann. Chem.,* 321-323.
7. W. Hummel, 1997, "New alcohol dehydrogenases for the synthesis of chiral compounds", *Adv. Biochem. Eng. Biotechnol.,* 58, 145-84.
8. M. J. Kim and G. M. Whitesides, 1988, "L-Lactate dehydrogenase: substrate specificity and use as a catalyst in the synthesis of homochiral 2-hydroxy acids", *J. Am. Chem. Soc.,* 110, 2959-64.
9. H. K. W. Kallwass, 1992, "Potential of R-2-hydroxyisocaproate dehydrogenase from *Lactobacillus casei* for stereospecific reductions", *Enzyme Microb. Technol.,* 14, 28-35.
10. G. Krix, A. S. Bommarius, K. Drauz, M. Kottenhahn, M. Schwarm and M.-R. Kula, 1997, "Enzymatic reduction of α-keto acids leading to L-amino acids or D-hydroxy Acids", *J. Biotechnology,* 53, 29-39.
11. Y. Asano, A. Yamada, Y. Kato, K. Yamaguchi, Y. Hibino, K. Hirai and K. Kondo, 1990, "Enantioselective synthesis of (S)-amino acids by phenylalanine dehydrogenase from *Bacillus sphaericus*: Use of natural and recombinant enzymes", *J. Org. Chem.,* 55, 5567-5571.
12. C. W. Bradshaw, C. H. Wong, W. Hummel and M.-R. Kula, 1991, "Enzyme-catalyzed asymmetric synthesis of (S)-2-amino-4-phenylbutanoic acid and (R)-2-hydroxy-4-phenylbutanoic acid", *Biorg. Chem.,* 19, 29-39.
13. R. L. Hanson, J. M. Howell, T. L. LaPorte, M. J. Donovan, D. L. Cazzulino, V. V. Zannella, M. A. Montana, V. B. Nanduri, S. R. Schwarz, R. F. Eiring, S. C. Durand, J. M. Wasylyk, W. L. Parker, M. S. Liu, F. J. Okuniewicz, B. Chen, J. C. Harris, K. J. Natalie, K. Ramig, S. Swaminathan, V. W. Rosso, S. K. Pack, B. T. Lotz, P. J. Bernot, A. Rusowicz, D. A. Lust, K. S. Tse, J. J. Venit, L. J. Szarka, and R. N. Patel, 2000, "Synthesis of allysine ethylene acetal using phenylalanine dehydrogenase from *Thermoactinomyces intermedius*", *Enzyme Microb Technol,* 26, 348-358.
14. R. L. Hanson, M. D. S., A. Banerjee, D. B. Brzozowski, B.-C. Chen, B. P. Patel, C. G. McNamee, G. A. Kodersha, D. R. Kronenthal, R. N. Patel and L. J. Szarka, *Bioorganic & Medicinal Chemistry* 1999, 7, 2247-2252.
15. A. Willetts, 1997, "Structural studies and synthetic applications of Baeyer-Villiger monooxygenases", *Trends Biotechnol.,* 15, 55-62.
16. M.-R. Kula, 1994, "Enzyme catalyzed reductions of carbonyl groups", Chiral Europe, Nice, France, Spring Innovations, Ltd., Stockport UK.
17. H. K. Chenault, G. M. Whitesides, *Appl. Biochem. Biotechnol.* 1987, 14, 147-97.
18. C. Wandrey, in: *Proceedings of the 4th European Congress on Biotechnology* (eds.: O. M. Neijssel, R. R. van der Meer, and K. Ch. A. M. Luyben), Amsterdam, 1987, vol. 4, 171-188.
19. E. Keinan, K. K. Seth, R. J. Lamed, *Ann. NY Acad. Sciences* (Enzyme Engineering 8) 1987, 501, 130-150.
20. W. Hummel, M.-R. Kula, *Eur. J. Biochem,* 1989, 184, 1-13.
21. R. Wichmann, C. Wandrey, A. F. Bueckmann, M.-R. Kula, *J. Biotechnol,* 1981, 23, 2789-2802.
22. U. Kragl, D. Vasic-Racki, C. Wandrey, *Chem. Ing. Tech,* 1992, 64, 499-509.
23. A. S. Bommarius, *Habilitation thesis*, RWTH Aachen, Aachen, Germany, 2000.
24. V. I. Tishkov, A. G. Galkin, V. V. Fedorchuk, P. A. Savitsky, A. M. Rojkova, H. Gieren, M.-R. Kula, *Biotechnol. Bioeng.* 1999, 64, 187-93.
25. K. Seelbach, B. Riebel, W. Hummel, M.-R. Kula, V. I. Tishkov, A. M. Egorov, C. Wandrey, U. Kragl, *Tetrahedron Letters* 1996, 37, 1377-80.
26. C.-H. Wong, G. M. Whitesides, *J. Amer. Chem. Soc.* 1981, 103, 4890-4899.
27. C.-H. Wong, D. G. Drueckhammer, *Biotechnology* 1985, 3, 649-651.
28. D. G. Drueckhammer, *PhD Thesis*, Texas A and M Univ., College Station/TX, USA, 1987.
29. M. Kataoka, L. P. Rohani, K. Yamamoto, M. Wada, H. Kawabata, K. Kita, H. Yanase, S. Shimizu, *Appl. Microbiol. Biotechnol.* 1997, 48, 699-703.
30. R. P. Ross, A. Claiborne, *J. Mol. Biol.* 1992, 227, 658-71.
31. J. Matsumoto, M. Higushi, M. Shimada, Y. Yamamoto, Y. Kamio, *Biosci. Biotechnol. Biochem.* 1996, 60, 39-43.
32. D. E. Ward, C. J. Donnelly, M. E. Mullendore, J. van der Oost, W. M. de Vos, and E. J. Crane 3rd, *Eur. J. Biochem.* 2001, 268, 5816-23.
33. Y. Yamamoto, Y. Kamio, Tanpakushitsu Kakusan Koso 2001, 46, 726-32.
34. B. R. Riebel, P. R. Gibbs, W. B. Wellborn, A. S. Bommarius, *Adv. Synth. Cat.* 2002, 344, 1156-1169.
35. W. Hummel and M.-R. Kula, 1989, "Dehydrogenases for the synthesis of chiral compounds", *Eur. J. Biochem.,* 184, 1-13.
36. T. Ohshima and K. Soda, 1990, "Biochemistry and biotechnology of amino acid dehydrogenases", *Adv. Biochem. Eng./Biotech.,* 42, 187-209.
37. W. Hummel, "Large-scale applications of NAD(P)-dependent oxidoreductases: recent developments", *TIBTECH* 1999, 17, 487-492.
38. R. Wichmann, C. Wandrey, A. F. Bückmann and M.-R. Kula, 1981, "Continuous enzymatic transformation in an enzyme membrane reactor with simultaneous NADH regeneration", *Biotechnol. Bioeng.,* 23, 2789-2802.
39. M.-R. Kula and C. Wandrey, 1987, "Continuous enzymatic transformation in an enzyme-membrane-reactor with simultaneous NADH regeneration", Meth. Enzymol. 136, 9-21.
40. G. L. Lemiére, J. A. Lepoivre and F. C. Alderweireldt, 1985, "HLAD-catalyzed oxidations of alcohols with acetaldehyde as a coenzyme recycling substrate", *Tetrahedron Lett.,* 26, 4527-28.
41. a) M. D. Bednarski, H. K. Chenault, E. S. Simon and G. M. Whitesides, 1987, "Membrane-enclosed enzymic catalysis (MEEC): a useful, practical new method for the manipulation of enzymes in organic synthesis", J. Amer. Chem. Soc., 109, 1283-85; b) H. K. Chenault and G. M. Whitesides, 1989, "Lactate dehydrogenase-catalyzed regeneration of NAD from NADH for use in enzyme-catalyzed synthesis", *Bioorg. Chem.,* 17, 400-9.
42. G. Carrea, R. Bovara, R. Longhi and S. Riva, 1985, "Preparation of 12-ketochenodeoxycholic acid from cholic acid using coimmobilized 12α-hydroxysteroid 43. L. G. Lee and G. M. Whitesides, 1985, "Enzyme-catalyzed organic synthesis: a comparison of strategies for in situ regeneration of NAD from NADH", *J. Am. Chem. Soc.*, 107, 6999-7008.
44. H. J. Park, C. O. Reiser, S. Kondruweit, H. Erdmann, R. D. Schmid and M. Sprinzl, 1992, "Purification and characterization of a NADH oxidase from the thermophile *Thermus thermophilus* HB8", *Eur. J. Biochem.*, 205, 881-5.
45. R. E. Altomare, J. Kohler, P. F. Greenfield and J. R. Kittrell, 1974, "Deactivation of immobilized beef liver catalase by hydrogen peroxide", *Biotechnol. Bioeng.*, 16, 1659-73.
46. K. Koike, T. Kobayashi, S. Ito and M. Saitoh, 1985, "Purification and characterization of NADH Oxidase from a strain of *Leuconostoc* meserentoides", *J. Biochem.*, 97, 1279-1288.
47. R. P. Ross and A. Claiborne, 1991, "Cloning, sequence and overexpression of NADH peroxidase from *Streptococcus faecalis* 10C1. Structural relationship with the flavoprotein disulfide reductases", *J. Mol. Biol.*, 221, 857-871.
48. R. P. Ross and A. Claiborne, 1992, "Molecular Cloning and Analysis of the Gene Encoding the NADH-Oxidase from *Streptococcus faecalis* 10C1. Comparison with NADH-Peroxidase and the Flavoprotein Disulfide Reductases", *J. Mol. Biol.*, 227, 658-671.
49. S. N. Peterson, P. C. Hu, K. F. Bott and C. A. Hutchinson 3rd, 1993, "A survey of the *Mycoplasma genitalium* genome by using random sequencing", *J. Bacteriol.*, 175, 7918-7930.
50. J. Matsumoto, M. Higushi, M. Shimada, Y. Yamamoto and Y. Kamio, 1996, "Molecular cloning and sequence analysis of the gene encoding the H2O-Forming NADH Oxidase from *Streptococcus mutans*", *Biosci. Biotech. Biochem.*, 60, 39-43.
51. C. J. Bult, O. White, G. J. Olsen, L. Zhou, R. D. Fleischmann, G. G. Sutton, J. A. Blake, L. M. FitzGerald, R. A. Clayton, J. D. Gocayne, A. R. Kerlavage, B. A. Dougherty, J. F. Tomb, M. D. Adams, C. I. Reich, R. Overbeek, E. F. Kirkness, K. G. Weinstock, J. M. Merrick, A. Glodek, J. L. Scott, N. S. Geoghagen, J. C. Venter, 1996, "Complete genome sequence of the methanogenic archaeon, *Methanococcus jannaschii*", *Science*, 273, 1058-1073.
52. V. Natarajan, S. M. Cramer, *J. Chromatography* A 2000, 876, 63-73.
53. A. Kundu, S. Vunnum, S. M. Cramer, *J. Chromatography* A 1995, 707, 57-67.
54. W. Hummel, *Adv. Biochem. Eng.* 1997, 58, 145-184.
55. B. Riebel, W. Hummel, A. Bommarius, Eur. Pat. Appl. EP 1,176,203, 2002.
56. W. Hummel, *Trends Biotechnol*, 1999, 17, 487-92.
57. B. Riebel, *PhD thesis*, University of Düsseldorf, Düsseldorf, Germany, 1997.
58. M. Wolberg, W. Hummel, M. Mueller, *Chemistry* 2001, 7, 4562-71.
59. J. Haberland, A. Kriegesmann, E. Wolfram, W. Hummel, A. Liese, *Appl. Microbiol Biotechnol*, 2002, 58, 595-9.
60. S. Lindsay, D. Brosnahan and G. D. Watt, 2001, "Hydrogen peroxide formation during iron deposition in horse spleen ferritin using O2 as an oxidant", *Biochemistry*, 40, 3340-7.
61. M. Zhou, Z. Diwu, N. Panchuk-Voloshina, R. P. Haugland, 1997, "A stable nonfluorescent derivative of resorufin for the fluorometric determination of trace hydrogen peroxide: applications in detecting the activity of phagocyte NADPH oxidase and other oxidases", *Anal. Biochem.*, 253, 162-168.
62. J. G. Mohanty, J. S. Jaffe, E. S. Schulman and D. G. Raible, 1997, "A highly sensitive fluorescent micro-assay of H2O2 release from activated human leukocytes using a dihydroxyphenoxazine derivative", *J. Immunol. Methods*, 202, 133-141.
63. R. K. Scopes, "Protein purification: principles and practice", Springer, New York, $3^{rd}$ edition, 1994.
64. B. R. Riebel, P. R. Gibbs, W. B. Wellborn and A. S. Bommarius, "Cofactor regeneration of NAD+ from NADH: novel water-forming NADH oxidases", *Adv. Synth. Catal.* 2002, 344, 1156-1168.
65. B. R. Riebel, P. R. Gibbs, W. B. Wellborn and A. S. Bommarius, Cofactor regeneration of both NAD+ from NADH and NADP+ from NADPH: NADH oxides from *Lactobacillus sanfranciscensis*", *Adv. Synth. Catal.* 2003, 345, 707-712.
66. Woodyer R D, Wymer N J, Racine F M, Khan S N & Saha B C (2008) Efficient production of L-ribose with a recombinant *Escherichia coli* biocatalyst. *Appl Environ Microb* 74, 2967-2975, doi: Doi 10.1128/Aem.02768-07.
67. Odman P, Wellborn W B & Bommarius A S (2004) An enzymatic process to alpha-ketoglutarate from L-glutamate: the coupled system L-glutamate dehydrogenase/NADH oxidase. *Tetrahedron-Asymmetr* 15, 2933-2937, doi: DOI 10.1016/j.tetasy.2004.07.055.
68. Jiang R R, Riebel B R & Bommarius A S (2005) Comparison of alkyl hydroperoxide reductase (AhpR) and water-forming NADH oxidase from *Lactococcus lactis* ATCC 19435. *Adv Synth Catal* 347, 1139-1146, doi: DOI 10.1002/adsc.200505063.
69. Stoop J M H, Williamson J D, Conkling M A, MacKay J J & Pharr D M (1998) Characterization of NAD-dependent mannitol dehydrogenase from celery as affected by ions, chelators, reducing agents and metabolites. *Plant Sci* 131, 43-51.

---

What is claimed is:

1. An isolated bacterial NADH oxidase, which is obtained from *Lactobacillus plantarum*, and regenerates NADP+ and NAD+, comprising
at least one amino acid mutation that facilitates enzymatic activity towards NADPH and comprises an amino acid sequence selected from the group consisting of SEQ ID NO: 3, SEQ ID NO: 4, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 16, and SEQ ID NO: 17.

2. The isolated bacterial NADH oxidase of claim 1, encoded by a nucleic acid sequence, which hybridizes under stringent conditions to the nucleic acid selected from the group consisting of SEQ ID NO: 5, SEQ ID NO: 7, SEQ ID NO: 10, SEQ ID NO: 13, and SEQ ID NO: 18.

3. The isolated bacterial NADH oxidase of claim 1, which comprises SEQ ID NO: 8.

4. The isolated bacterial NADH oxidase of claim 3, encoded by a nucleic acid sequence comprising SEQ ID NO: 10.

5. The isolated bacterial NADH oxidase of claim 1, which comprises SEQ ID NO: 16.

6. The isolated bacterial NADH oxidase of claim 5, encoded by a nucleic acid sequence comprising SEQ ID NO: 18.

7. A method of producing an enantiomer-enriched organic compound, comprising:
reacting a substrate with a first enzyme selective for producing an enantiomer, wherein the first enzyme requires a oxidized nicotinamide-based cofactor for catalytic activity;
producing the enantiomer, its oxidized counterpart, and a reduced nicotinamide-based cofactor; and
oxidizing the reduced nicotinamide-based cofactor with a second enzyme selective for a nicotinamide-based cofactor,
wherein the second enzyme selective for a nicotinamide-based cofactor comprises an amino acid sequence selected from the group consisting of SEQ ID NO: 3, SEQ ID NO: 4, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 16, or SEQ ID NO: 17.

8. The method of producing an enantiomer-enriched organic compound of claim 7, wherein the enantiomer comprises an L-nucleoside, and wherein the second enzyme selective for a nicotinamide-based cofactor comprises a NADH oxidase obtained from *Lactobacillus plantarum*.

9. The method of producing an enantiomer-enriched organic compound of claim 7, wherein the second enzyme selective for a nicotinamide-based cofactor can oxidize NADPH and NADH.

10. The method of producing an enantiomer-enriched organic compound of claim 9, wherein the second enzyme selective for a nicotinamide-based cofactor comprises SEQ ID NO: 8.

11. The method of producing an enantiomer-enriched organic compound of claim 9, wherein the second enzyme selective for a nicotinamide-based cofactor comprises SEQ ID NO: 18.

12. The method of producing an enantiomer-enriched organic compound of claim 7, wherein the second enzyme selective for a nicotinamide-based cofactor can catalyze more than 113,000 turnovers per active site.

13. The method of producing an enantiomer-enriched organic compound of claim 7, wherein the second enzyme selective for a nicotinamide-based cofactor can catalyze more than 100,000 turnovers per active site in the absence of an externally added reducing agent.

* * * * *